（12） United States Patent
Pierce et al.

(10) Patent No.: US 7,727,721 B2
(45) Date of Patent: * Jun. 1, 2010

(54) HYBRIDIZATION CHAIN REACTION AMPLIFICATION FOR IN SITU IMAGING

(75) Inventors: Niles A. Pierce, Pasadena, CA (US); Robert Dirks, Pasadena, CA (US); Scott E. Fraser, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 11/371,346

(22) Filed: Mar. 7, 2006

(65) Prior Publication Data

US 2006/0228733 A1    Oct. 12, 2006

Related U.S. Application Data

(60) Provisional application No. 60/659,499, filed on Mar. 8, 2005.

(51) Int. Cl.
   *C12Q 1/68*    (2006.01)
(52) U.S. Cl. .......................................... 435/6
(58) Field of Classification Search ........ 435/6
   See application file for complete search history.

(56) References Cited

U.S. PATENT DOCUMENTS

| | | |
|---|---|---|
| 4,714,680 A | 12/1987 | Civin |
| 4,897,355 A | 1/1990 | Eppstein et al. |
| 4,965,204 A | 10/1990 | Civin |
| 5,057,410 A | 10/1991 | Kawasaki et al. |
| 5,061,620 A | 10/1991 | Tsukamoto et al. |
| 5,459,127 A | 10/1995 | Felgner et al. |
| 5,579,793 A | 12/1996 | Gajewski et al. |
| 5,643,741 A | 7/1997 | Tsukamoto et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,928,913 A | 7/1999 | Efstathiou et al. |
| 5,989,823 A | 11/1999 | Jayasena et al. |

(Continued)

FOREIGN PATENT DOCUMENTS

EP    0273085    7/1988

(Continued)

OTHER PUBLICATIONS

U.S. Appl. No. 11/371,347, filed Mar. 7, 2006, Pierce et al.

(Continued)

*Primary Examiner*—Kenneth R. Horlick
(74) *Attorney, Agent, or Firm*—Knobbe, Martens, Olson & Bear, LLP

(57) ABSTRACT

The present invention relates to the use of fluorescently labeled nucleic acid probes to identify and image analytes in a biological sample. In the preferred embodiments, a probe is provided that comprises a target region able to specifically bind an analyte of interest and an initiator region that is able to initiate polymerization of nucleic acid monomers. After contacting a sample with the probe, labeled monomers are provided that form a tethered polymer. Triggered probes and self-quenching monomers can be used to provide active background suppression.

18 Claims, 13 Drawing Sheets

U.S. PATENT DOCUMENTS

| | | | |
|---|---|---|---|
| 6,242,246 | B1 | 6/2001 | Gold et al. |
| 6,261,783 | B1 | 7/2001 | Jayasena et al. |
| 6,361,944 | B1 | 3/2002 | Mirkin et al. |
| 6,361,945 | B1 * | 3/2002 | Becker et al. ............... 435/6 |
| 6,485,965 | B1 | 11/2002 | Klatzmann et al. |
| 6,506,559 | B1 | 1/2003 | Fire et al. |
| 6,555,367 | B1 | 4/2003 | Spence et al. |
| 6,899,871 | B2 | 5/2005 | Kasahara et al. |
| 7,033,834 | B2 | 4/2006 | Valerio et al. |
| 2002/0051769 | A1 | 5/2002 | Zhang |
| 2002/0172950 | A1 | 11/2002 | Kenny et al. |
| 2003/0092162 | A1 | 5/2003 | Shankara et al. |
| 2004/0223953 | A1 | 11/2004 | Kung et al. |
| 2005/0260635 | A1 | 11/2005 | Dirks et al. |
| 2006/0234261 | A1 | 10/2006 | Pierce et al. |

FOREIGN PATENT DOCUMENTS

| | | |
|---|---|---|
| WO | WO 94/01550 | 1/1994 |
| WO | WO 99/31276 | 6/1999 |

OTHER PUBLICATIONS

Bushnell et al., "ProbeDesigner: for the design of probesets for branched DNA (bDNA) signal amplification assays," Bioinformatics, 15(5):348-355, 1999.

Collins et al., "A branched DNA signal amplification assay for quantification of nucleic acid targets below 100 molecules/ml," Nucleic Acids Res, 25(15):2979-2984, 1997.

van de Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, 46(11):1249-1259, 1998.

Dirks et al., "Paradigms for computational nucleic acid design," Nucleic Acids Research, 2004, pp. 1392-1403, vol. 32, No. 4, Oxford University Press 2004.

Dirks et al., "Triggered amplification by hybridization chain reaction," PNAS, Oct. 26, 2004, pp. 15275-15278, vol. 101, No. 43.

Elghanian et al.,"Selective colorimetric detection of polynucleotides based on the distance-dependent optical properties of gold nanoparticles," Science, 277(5329):1078-1081,1997.

Ellington et al., "In vitro selection of RNA molecules that bind specific ligands," Nature 346:818-822, 1990.

Flamm et al., "RNA folding at elementary step resolution," RNA, 2000, pp. 325-338, vol. 6, Cambridge University Press.

Hofacker et al., "Fast folding and comparison of RNA secondary structures," Monatshefte für Chemie, 1994, pp.167-188, vol. 125.

Hughes et al., "Double Labeling wit Fluorescence In Situ Hybridization in Drosophila Whole-Mount Embryos," BioTechniques, 24(4):530-532, 1998.

Huizenga et al., "A DNA Aptamer That Binds Adenosine and ATP," Biochemistry 34:656-665 (1995.

Iqbal et al., "A review of molecular recognition technologies for detection of biological threat agents", Biosensors & Bioelectronics, 2000, pp. 549-578, vol. 15.

Kislauskis et al. "Isoform-specific 3'-untranslated Sequences Sort α-cardiac and β-cytoplasmic Actin Mesenger RNAs to Different ytoplasmic Compartments," The Journal of Cell Biology, 123(1):165 172, 1993.

Kosman, et al., "Multiplex Detection of RNA Expression in Drosophila Embryos," Science, 305:846, 2004.

Lawrence et al., "Highly Localized Tracks of Specific Transcripts within Interphase Nuclei Visualized by In Situ Hybridication," Cell, 57:493-502, 1989.

Levsky et al., "Single-Cell Gene Expression Profiling," Science 297:836-840,2002.

Liu et al., "A colorimetric lead biosensor using DNAzyme-directed assembly of gold nanoparticles," J. Am. Chem. Soc., 125(22):6642-6643, 2003.

Macechko et al., "Comparison of Immunologic Amplification vs Enzymatic Deposition of Fluorochrome-conjugated Tyramide as Detection Systems for FISH," J Histochem Cytochem, 45(3):359-363, 1997.

Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, 2002, pp. 14281-14292, vol. 41, American Chemical Society.

Nutiu et al., "Structure-switching signaling aptamers," J. Am. Chem. Soc., 2003, pp. 4771-4778, vol. 125, American Chemical Society.

Player et al., "Single-copy Gene Detection Using Branched DNA (bDNA)) In Situ Hybridization," J. Histochem & Cytochem, 49(5):603-611, 2001.

Qian et al., "Recent Developments in Signal Amplification Methods for In Situ Hybridization," Diagnostic Molecular Pathology, 12(1):1-13, 2003.

Rachofsky et al., "Probing structure and dynamics of DNA with 2-aminopurine: Effects of local environment on fluorescence," Biochemistry, 2001, pp. 946-956, vol. 40.

Schweitzer et al., "Combining nucleic acid amplification and detection," Curr Opin Biotechnol, 12:21-27, 2001.

Seeman, "Nucleic acid junctions and lattices," J. Theor. Biol., 1982, pp. 237-247, vol. 99, Academic Press Inc. (London) Ltd.

Storhoff et al., "One-pot colorimetric differentiation of polynucleotides with single base imperfections using gold nanoparticles," J. Am. Chem. Soc., 120:1959-1964, 1998.

Tuerk et al., "Systematic Evolution of Ligands by Exponential Enrichment: RNA Ligands to Bacteriophage T4 DNA Polymerase," Science 249:505-510, 1990.

Tyagi et al., "Molecular Beacons: Probes that Fluoresce upon Hybridization," Nature Biotechnology 14:303-308, 1996.

Wilkie et al., "Transcribed genes are localized according to chromosomal position within polarized Drosophila embryonic nuclei," Current Biology, 9:1263-1266, 1999.

Zuker et al., "Optimal computer folding of large RNA sequence using thermodynamics and auxiliary information," Nucleic Acids Research, vol. 9, No. 1, pp. 133-147 (1981).

"The Handbook—A Guide to Fluorescent Probes And Labeling Technologies,"10th Ed. (available at http://www.probes.com).

Dirks et al., "Triggered amplification by hybridization chain reaction," PNAS, vol. 101, No. 43, pp. 15275-15278, Oct. 26, 2004.

Turberfield et al., "DNA Fuel for Free-Running Nanomachines," Physical Review Letters, The American Physical Society, vol. 90, No. 11, pp. 118102-1-118102-4, Mar. 21, 2003.

Völker et al., "Conformational energetics of stable and metastable states formed by DNA triplet repeat oligonucleotides: Implications for triplet expansion diseases," PNAS, vol. 99, No. 23, pp. 14700-14705, Nov. 12, 2002.

Amarzguioui et al., "Rational design and in vitro and in vitro delivery of Dicer substrate siRNA,", Nature Protocols, vol. 1, No. 2, pp. 508-517, 2006.

Bois et al., "Topological constraints in nucleic acid hybridization kinetics," Nucleic Acids Research, vol. 33, No. 13, pp. 4090-4095, 2005.

Definition for "substantial" from Merriam-Webster Online Dictionary. Downloaded from Merriam-Webster.com on Mar. 5, 2008.

Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.

Elbashir et al., "Functional anatomy of siRNAs for mediating efficient RNAi in Drosophila melanogaster embryo lysate", The EMBO Journal, vol. 20, No. 23, pp. 6877-6888, 2001.

Felgner, et al., "Nomenclature for Synthetic Gene Delivery Systems", Human Gene Therapy, vol. 8, pp. 511-512, Mar. 20, 1997.

Ferkol et al., "Gene Transfer into the Airway Epithelium of Animals by Targeting the Polymeric Immunoglobulin Receptor", J. Clin. Invest., vol. 95, pp. 493-502, Feb. 1995.

Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.

Fire et al., "Potent and specific genetic interference by double-stranded RNA in *Caenorhabditis elegans*", Nature, vol. 391, pp. 806-811, Feb. 19, 1998.

Friedrich et al., "RNA molecules as anti-cancer agents", Seminars in Cancer Biology, vol. 14, pp. 223-230, 2004.

Friedrich et al., A Cellular Screening Assay to Test the Ability of PKR to Induce Cell Death in Mammalian Cells, Molecular Therapy, vol. 12, No. 5, pp. 969-975, Nov. 2005.

Heidel, J.D., "Targeted, systematic non-viral delivery of small interfering RNA in vivo", Doctoral thesis, California Institute of Technology, pp. 1-128, 2005.

Jhaveri et al., "In vitro selection of signaling aptamers", Nature Biotechnology, vol. 18, pp. 1293-1297, Dec. 2000.

Kim et al., "Synthetic dsRNA Dicer substrates enhance RNAi potency and efficacy", Nature Biotechnology, vol. 23, No. 2, pp. 222-226, Feb. 2005.

Ladiges, et al., "Tissue specific expression of PKR protein kinase in aging B6D2F1 mice," Mechanisms of Ageing and Development, vol. 114, pp. 123-132, (2000).

Mahato et al., "Modulation of gene expression by antisense and antigene oligodeoxynucleotides and small interfering RNA", Expert Opin. Drug Deliv., vol. 2, No. 1, pp. 3-28. 2005.

Manche et al., "Interactions between Double-Stranded RNA Regulators and the Protein Kinase DAI", Molecular and Cellular Biology, vol. 12, No. 11, pp. 5238-5248, Nov. 1992.

Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.

Mittelstadt, et al., "Interaction of human tRNA-dihydrouridine synthase-2 with interferon-induced protein kinase PKR," Nucleic Acids Research, vol. 36, No. 3, pp. 998-1008, (2008).

Park et al., "Rapid Identification of *Candida dubliniensis* Using a Species-Specific Molecular Beacon", Journal of Clinical Microbiology, vol. 38, No. 8, pp. 2829-2836, 2000.

Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.

Scherer et al., "Approaches for the sequence-specific knockdown of mRNA", Nature Biotechnology, vol. 21, No. 12, pp. 1457-1465, 2003.

Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.

Seelig et al., "Catalyzed Relaxation of a Metastable DNA Fuel", Journal American Chemical Society, vol. 128, No. 37, pp. 12211-12220, 2006.

Shir et al., "Inhibition of glioma growth by tumor-specific activation of double-stranded RNA-dependent protein kinase PKR", Nature Biotechnology, vol. 20, pp. 895-900, Sep. 2002.

Sokol et al., "Real time detection of DNA•RNA hybridization in living cells", Proc. Natl. Acad. Sci. USA, Vol. 95, pp. 11538-11543, Sep. 1998.

Tijsterman et al., "Dicers at RISC: The Mechanism of RNAi", Cell, vol. 117, pp. 1-3, 2004.

Vermeulen et al., "The contributions of dsRNA structure to Dicer specificity and efficiency", RNA, vol. 11, pp. 674-682, 2005.

Wagner et al., "Transferrin-Polycation Conjugates as Carriers for DNA Uptake into Cells", Proceedings of the National Academy of Sciences of the United States of America, vol. 87, pp. 3410-3414, May 1990.

Williams, B.R.G., "PKR; a sentinel kinase for cellular stress", Oncogene, vol. 18, pp. 6112-6120, 1999.

Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.

Wu et al., "Receptor-mediated in Vitro Gene Transformation by a Soluble DNA Carrier System", The Journal of Biological Chemistry, vol. 262, No. 10, pp. 4429-4432, 1987.

Yin et al., "Programming biomolecular self-assembly pathways", Nature, vol. 451, pp. 318-323, Jan. 17, 2008.

Zheng et al., "Activation of the protein kinase PKR by short double-stranded RNAs with single-stranded tails", RNA, vol. 10, pp. 1934-1945, 2004.

International Search Report and Written Opinion from PCT/US2005/009471, dated Mar. 8, 2006.

Supplementary European Search Report from PCT/US2005/009471, dated May 6, 2008.

U.S. File History printed Jun. 16, 2009 for U.S. Appl. No. 11/087,937, filed Mar. 22, 2005, entitled "Hybridization Chain Reaction."

U.S. File History printed Jun. 16, 2009 for U.S. Appl. No. 11/371,347, filed Mar. 7, 2006, entitled "Colorimetric Readout of Hybridization Chain Reaction."

U.S. File History printed Jun. 16, 2009 for U.S. Appl. No. 11/544,306, filed Oct. 6, 2006, entitled "PKR Activation Via Hybridization Chain Reaction."

U.S. File History printed Jun. 16, 2009 for U.S. Appl. No. 12/040,735, filed Feb. 29, 2008, entitled "Triggered RNAi."

U.S. File History printed Jun. 16, 2009 for U.S. Appl. No. 12/152,893, filed May 16, 2008, entitled "A Versatile Nucleic Acid Hairpin Motif for Programming Biomolecular Self-Assembly Pathways."

* cited by examiner

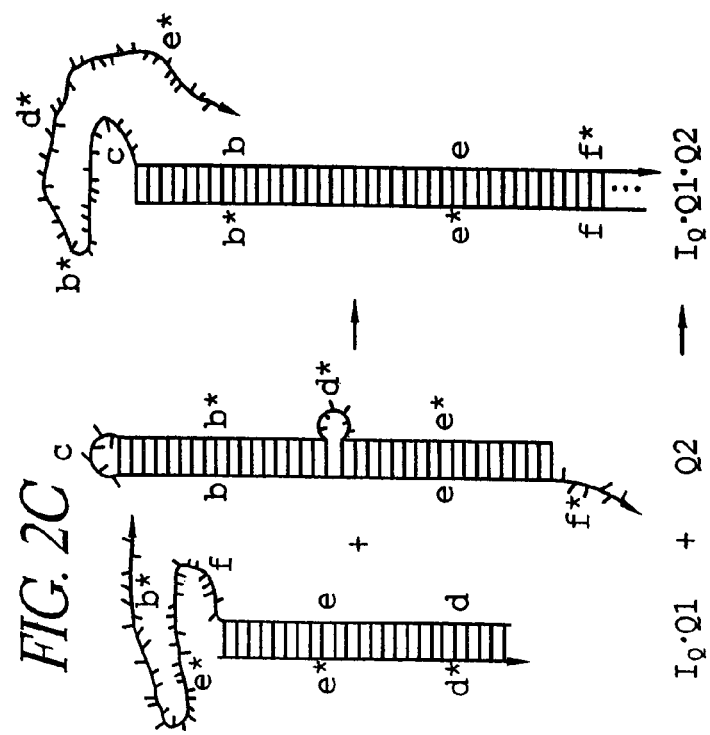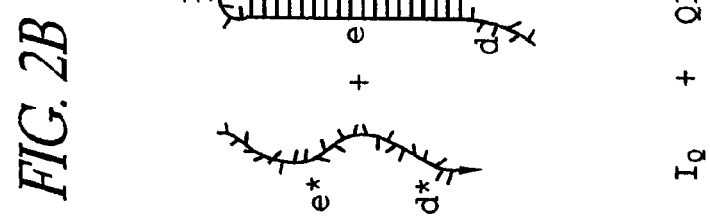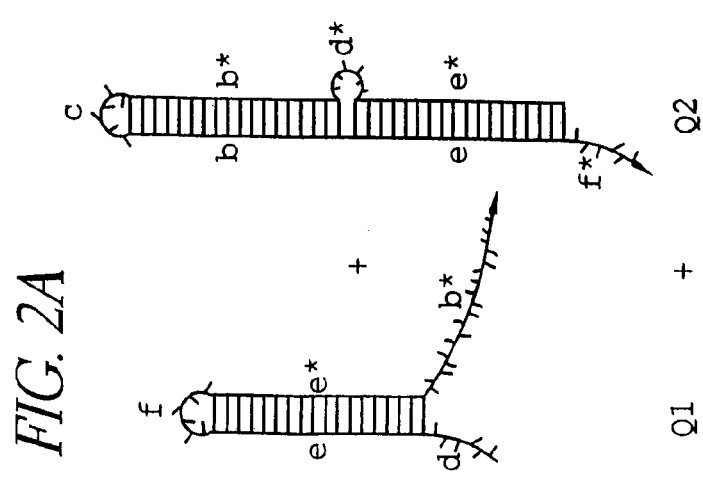

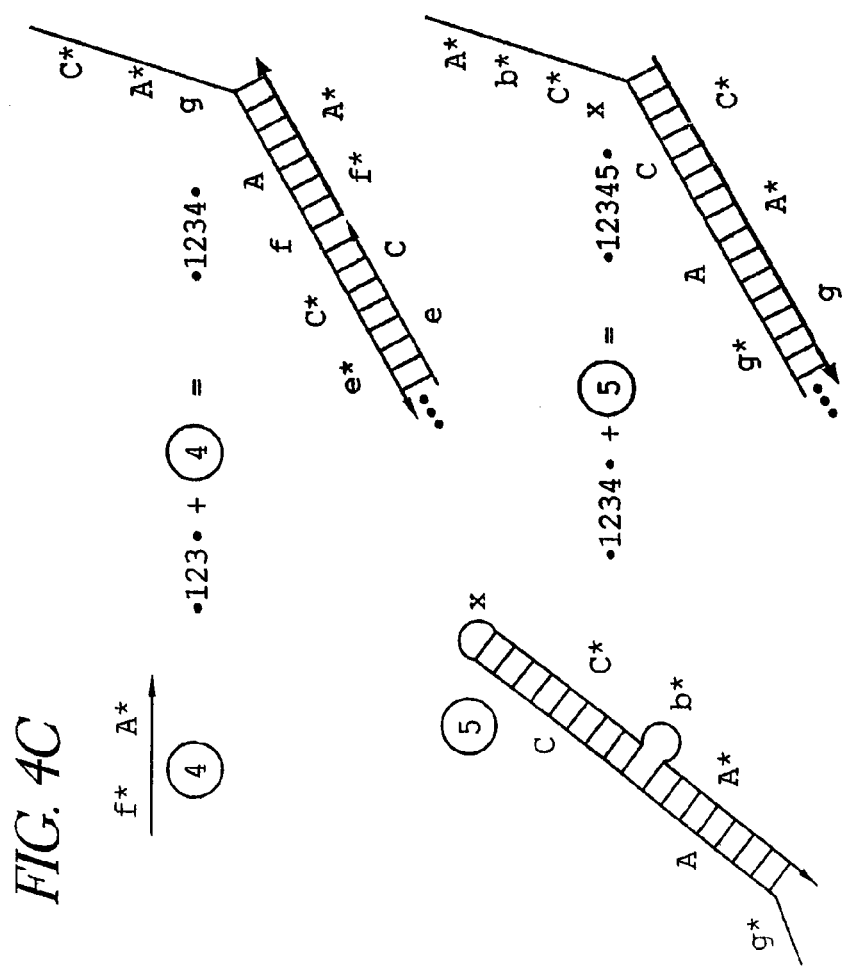
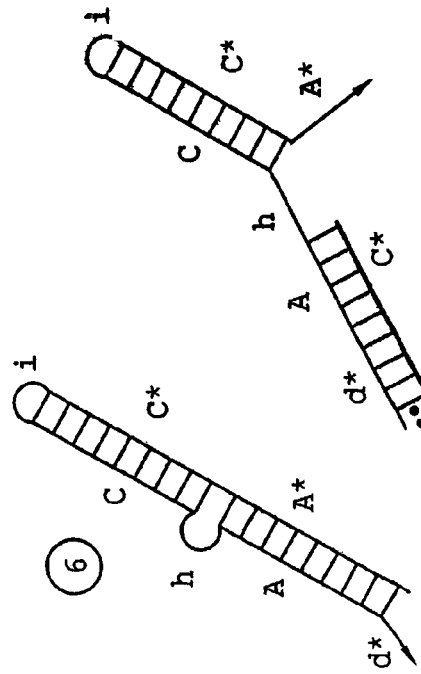
FIG. 4C
FIG. 4D

SEQUENCE LISTING

```
<160> NUMBER OF SEQ ID NOS: 7

<210> SEQ ID NO 1
<211> LENGTH: 48
<212> TYPE: DNA
<213> ORGANISM: Artificial Sequence
<220> FEATURE:
<223> OTHER INFORMATION: DNA Oligomer

<400> SEQUENCE: 1
ttaacccacg ccgaatccta gactcaaagt agtctaggat tcggcgtg                  48

<210> SEQ ID NO 2
<211> LENGTH: 48
<212> TYPE: DNA
<213> ORGANISM: Artificial Sequence
<220> FEATURE:
<223> OTHER INFORMATION: DNA Oligomer

<400> SEQUENCE: 2
agtctaggat tcggcgtggg ttaacacgcc gaatcctaga ctactttg                  48

<210> SEQ ID NO 3
<211> LENGTH: 24
<212> TYPE: DNA
<213> ORGANISM: Artificial Sequence
<220> FEATURE:
<223> OTHER INFORMATION: DNA Oligomer

<400> SEQUENCE: 3
agtctaggat tcggcgtggg ttaa                                            24

<210> SEQ ID NO 4
<211> LENGTH: 48
<212> TYPE: DNA
<213> ORGANISM: Artificial Sequence
<220> FEATURE:
<223> OTHER INFORMATION: DNA Oligomer

<400> SEQUENCE: 4
catctcggtt tggctttctt gttacccagg taacaagaaa gccaaacc                  48

<210> SEQ ID NO 5
<211> LENGTH: 48
<212> TYPE: DNA
<213> ORGANISM: Artificial Sequence
<220> FEATURE:
<223> OTHER INFORMATION: DNA Oligomer

<400> SEQUENCE: 5
taacaagaaa gccaaaccga gatgggtttg gctttcttgt tacctggg                  48

<210> SEQ ID NO 6
<211> LENGTH: 58
<212> TYPE: DNA
<213> ORGANISM: Artificial Sequence
<220> FEATURE:
```

```
<223> OTHER INFORMATION: DNA Oligomer

<400> SEQUENCE: 6
cccaggtaac aagaaagcca aacctcttgt tacctggggg agtattgcgg aggaaggt        58

<210> SEQ ID NO 7
<211> LENGTH: 24
<212> TYPE: DNA
<213> ORGANISM: Artificial Sequence
<220> FEATURE:
<223> OTHER INFORMATION: DNA Oligomer

<400> SEQUENCE: 7
cccaggtaac aagaaagcca aacc                                            24
```

HYBRIDIZATION CHAIN REACTION AMPLIFICATION FOR IN SITU IMAGING

REFERENCE TO RELATED APPLICATIONS

The present application claims priority to U.S. Provisional Application No. 60/659,499, filed Mar. 8, 2005, which is herby incorporated by reference in its entirety.

STATEMENT REGARDING FEDERALLY SPONSORED R&D

This invention was made with government support under grant nos. P01 HD037105, R01 HD043897, and R01 HL078691 awarded by the National Institutes of Health. The government has certain rights in the invention.

BACKGROUND OF THE INVENTION

1. Field of the Invention

The present invention relates generally to the use of hybridization chain reaction for in situ imaging.

2. Description of the Related Art

Hybridization Chain Reaction (HCR) is a novel method for the triggered chain of hybridization of nucleic acid molecules starting from stable, monomer hairpins or other more complicated nucleic acid structures. HCR is described in U.S. patent application Ser. No. 11/087,937, filed Mar. 22, 2005, which is incorporated herein by reference. In the simplest version of this process, stable monomer hairpins undergo a chain reaction of hybridization events to form a nicked helix when triggered by a nucleic acid initiator strand. The fundamental principle behind HCR is that short loops are resistant to invasion by complementary single-stranded nucleic acids. This stability allows for the storage of potential energy in the form of loops; potential energy is released when a triggered conformational change allows the single-stranded bases in the loops to hybridize with a complementary strand. HCR is described in co-pending provisional patent application Ser. No. 60/556,147 filed on Mar. 25, 2004, incorporated herein by reference in its entirety, and one embodiment is illustrated in FIG. 1. A more complex embodiment, quadratic HCR, is shown in FIG. 2.

In situ hybridization methods enable the detailed spatial mapping of genes and mRNAs in normal and pathological tissues, allowing the study of gene expression and regulation in a morphological context from the sub-cellular to the organismal levels. Target nucleic acids are identified via the hybridization of nucleic acid probes that facilitate subsequent imaging by one of a number of methods. Radiolabeled probe molecules provide high sensitivity, but poor spatial resolution and the disadvantage of working with biohazardous materials has motivated the development of several nonradioactive alternatives. In situ biological imaging of an analyte (including not only nucleic acids, but proteins and other molecules and compounds) or multiple analytes can be accomplished by a variety of methods; however, such techniques have limitations, particularly as the number of analytes increases.

Fluorescence in situ hybridization (FISH) methods enable the detailed mapping of transcriptionally active genes from sub-cellular to organismal levels. (Lawrence et al. Cell, 57:493-502, 1989; Kislauskis et al. The Journal of Cell Biology, 123(1):165 172, 1993; Wilkie et al. Current Biology, 9: 1263-1266, 1999; Levsky, et al. Science 297:836-840, 2002; D. Kosman, et al. Science, 305:846, 2004.) Fluorescently-labeled nucleic acid probes are amenable to multiplexing (Levsky, 2002) but provide low sensitivity due to the small number of dyes per probe (Kosman, 2004). Immunological methods employ antibodies to bind haptenated nucleic acid probes which are then detected using fluorescently-labeled secondary antibodies (Kosman, 2004; Hughes et al. BioTechniques, 24(4):530-532, 1998). Some amplification can be achieved by introducing additional layers of labeled antibodies, (P. T. Macechko, et al. J Histochem Cytochem, 45(3):359-363, 1997) but the sensitivity is insufficient for imaging low-abundance mRNAs. Spatially localized signal amplification can be achieved using horseradish peroxidase-labeled antibodies (Wilkie, 1999; Kosman, 2004) or probes (M. P. C. van de Corput et al. J Histochem Cytochem, 46(11):1249-1259, 1998) to catalyze the binding of fluorescent tyramides in the vicinity of the probe. This approach significantly enhances sensitivity, but serial multiplexing results in sample degradation. Similar sensitivities have been achieved using in situ PCR, but the method is more cumbersome and the results are less reproducible. All of the above methods suffer from enhanced background signal due to the nonspecific binding of nucleic acid probes prior to fluorescent labeling or amplification.

Another technique for amplifying a signal from a hybridization event is the branched DNA (bDNA) approach, in which a pre-amplifier strand hybridizes to a portion of the probe, which in turn serves as a nucleation site for the hybridization of a fixed number of multiply-labeled amplifier strands. (Schweitzer et al. Curr Opin Biotechnol, 12:21-27, 2001.; Qian et al. Diagnostic Molecular Pathology, 12(1):1-13, 2003; Collinset al.. Nucleic Acids Res, 25(15):2979-2984, 1997.; Bushnell, et al. Bioinformatics, 15(5):348-355, 1999; Player, et al. J Histochem Cytochem, 49(5):603-611, 2001.)

SUMMARY OF THE INVENTION

Methods and compositions for detecting one or more analytes within a biological sample (in situ) using HCR are provided. The advantages of HCR for in situ imaging include, without limitation, the ability to rapidly amplify a signal based on a small amount of analyte present and the ability to image a diversity of analytes in the same sample.

In one aspect of the invention, methods are provided for detecting an analyte in a biological sample. Preferably, the sample is contacted with a probe comprising a target region and an initiation region. The target region is able to specifically bind to the analyte of interest, while the initiation region is able to initiate the polymerization of labeled nucleic acid monomers. Thus, the sample is contacted with a first metastable monomer comprising an initiator region that is complementary to the initiation region of the probe and a second metastable monomer comprising a region complementary to a portion of the first monomer. One or both of the monomers is preferably labeled with a fluorescent dye. They may also be labeled with a fluorescence quencher such that prior to polymerization the fluorescence is quenched. A fluorescent signal is thus generated upon formation of a polymer and background is reduced.

The analyte to be detected is not limited in any way and may be, for example, a nucleic acid such as mRNA or a gene of interest, or a polypeptide. In some preferred embodiments the analyte is a nucleic acid and the target region of the probe is complementary to at least a portion of the analyte.

In some embodiments, a triggered probe is utilized, such that the initiation region is only made available to interact with the monomers when the probe is bound to the analyte of interest. For example, in some embodiments the probe undergoes a conformational change upon binding of the target region to the analyte such that the initiation region is available to stimulate polymerization. In this way, non-specific polymerization resulting from non-specific probe binding is reduced.

The in situ HCR reactions can be multiplexed to identify the presence of multiple analytes of interest simultaneously.

In another aspect, methods of in situ imaging are provided in which a biological sample is contacted with a probe comprising a target region capable of specifically binding to an analyte of interest and an initiator region, such that the probe binds to the analyte of interest. The sample is then contacted with at least two fluorescently labeled monomers, whereby the initiator region of the bound probe hybridizes to at least one of the monomers. As a result, the monomers form a fluorescently labeled polymer tethered to the analyte via the probe. The fluorescently labeled polymer can then be visualized.

In a further aspect, kits are provided for the in situ detection of an analyte of interest, preferably a nucleic acid. The kits preferably comprise a first metastable nucleic acid monomer comprising an initiator complement region and a fluorescent label and a second metastable nucleic acid monomer comprising a propagation region that is substantially complementary to a portion of the first nucleic acid. A probe is included comprising a target region that is complementary to at least a portion of the nucleic acid to be detected and an initiator strand that is complementary to the initiator complement region of the first monomer. The first and second monomers are preferably hairpin monomers. In some embodiments the kits comprise one or more additional monomers and may comprise one or more additional probes, for identifying multiple analytes.

BRIEF DESCRIPTION OF THE DRAWINGS

FIG. 1 schematically illustrates one embodiment of an HCR system. Each letter represents a segment of nucleic acids. Letters marked with a * are complementary to the corresponding unmarked letter.

FIG. 2 illustrates an embodiment in which HCR utilizing two monomer pairs produces quadratic signal amplification. FIG. 2A illustrates two hairpin monomers Q1 and Q2 that are metastable in the absence of initiator IQ. As shown in FIG. 2B, binding of IQ leads to a strand displacement interaction that exposes sticky end fe*b*. This single stranded region then nucleates at the f* sticky end of Q2, and a subsequent branch migration exposes segments cb*d* and e* as shown in FIG. 2C. The d*e* region initiates the next Q1 molecule, leading to amplification in one direction, while the exposed cb* region initiates a second HCR reaction involving monomers H1 and H2 (FIG. 1).

FIGS. 4A-E illustrate another embodiment for HCR with exponential growth. Eight different strands are used in this embodiment. Strand one (1) is the 'hub' of the system and has an exposed, single-stranded region joining two hairpins (FIG. 4A). When the initiator (2) binds, it creates a long helix with one sticky end on each side. The two sticky ends generated by the initiated 'hub' bind with strands (3) and (6), respectively (FIGS. 4B and C). Next, auxiliary strands (4) and (7) bind to previously protected bulge loops (FIGS. 4D and E), and expose two hairpin regions. These hairpins then bind to strands (5) and (8), respectively, to generate sticky ends similar to the initiator molecule (2). Thus, each initiator produces two new initiators, leading to exponential growth. As a side note, two subsets of strands (1,2,3,4,5) and (1,2,6,7,8) produce linear systems in the absence of the other strands.

As shown in FIGS. 10A and C fluorescent end-labeling leads to fluorophores at ≈8 nm spacing in the assembled amplification polymers. Self-quenching hairpins (FIGS. 10B and D) with fluorophore/quencher pairs reduce the background signal further for in vivo applications, particularly where unused hairpins cannot be washed out of the sample. The fluorophore/quencher distance increases from ≈2 nm to ≈8 nm after HCR amplification polymers have assembled, leading to increased fluorescence.

FIG. 11A illustrates the HCR amplification components. Strand 1 corresponds to the initiator sequence that is exposed when a triggered probe binds specifically to its target. FIG. 11B illustrates a partially assembled branched amplification polymer. FIG. 11C shows a binary branching tree for an amplification polymer with four generations.

DETAILED DESCRIPTION

Figure 1A:
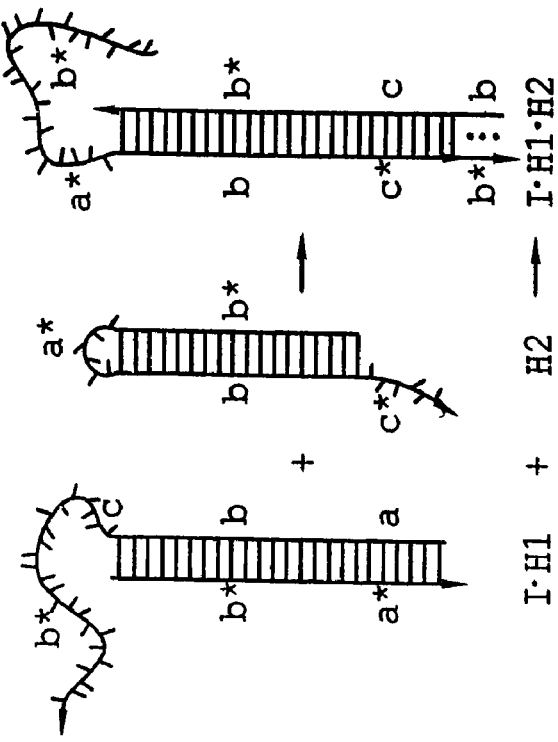
FIG. 1A shows two hairpins, labeled H1 and H2, that are metastable in the absence of initiator I. The hairpins comprise sticky ends 'a' and 'c*', respectively. Potential energy is stored in the hairpin loops.

Hybridization Chain Reaction (HCR) is a method for the triggered hybridization of nucleic acid molecules starting from metastable monomer hairpins or other metastable nucleic acid structures. See, for example, Dirks, R. and Pierce, N. Proc. Natl. Acad. Sci. USA 101(43): 15275-15278 (2004), and U.S. patent application Ser. No. 11/087,937, filed Mar. 22, 2005, each of which is incorporated herein by reference in its entirety. HCR does not require any enzymes and can operate isothermally.

In one embodiment of HCR, two or more metastable monomer hairpins are used. The hairpins preferably comprise loops that are protected by long stems. The loops are thus resistant to invasion by complementary single-stranded nucleic acids. This stability allows for the storage of potential energy in the loops. Potential energy is released when a triggered conformational change allows the single-stranded bases in the loops to hybridize with a complementary strand, preferably in a second hairpin monomer.

Each monomer is caught in a kinetic trap, preventing the system from rapidly equilibrating. That is, pairs of monomers are unable to hybridize with each other in the absence of an initiator. Introduction of an initiator strand causes the monomers to undergo a chain reaction of hybridization events to form a nicked helix (see FIGS. 1A-C). HCR can be used, for example, to detect the presence of an analyte of interest in a sample. This and other applications are discussed in more detail below.

Methods and compositions for detecting one or more analytes within a biological sample (in situ) using HCR are provided. The advantages of HCR for in situ imaging include, without limitation, the ability to rapidly amplify a signal based on a small amount of analyte present and the ability to image a diversity of analytes in the same sample.

As described herein the use of HCR for in situ detection and imaging provides a number of advantages. Specificity can be achieved by using triggered probes that protect the initiators until the probes bind specifically to targets. Self-quenching HCR monomers can be labeled with fluorophore/quencher pairs that become separated during self-assembly into tethered amplification polymers. This active background suppression is particularly useful for in vivo applications where unused amplification components cannot be washed away before imaging. Versatility can be achieved by selecting structure-switching aptamers (Ellinton et al. Nature 346:818-822, 1990 and Tuerk et al. Science 249:505-510, 1990) that generalize the triggered probe concept to the detection of proteins and small molecules. Small probe and amplification monomers, preferably with maximum dimensions of 8-16 nm facilitate sample penetration. Isothermal conditions are ideal for HCR amplification, avoiding damage to the morphology of fixed samples or their components and facilitating in vivo imaging. Multiplexing follows naturally from the use of independent HCR amplifiers that operate simultaneously, for example using spectrally distinct fluorophores to encode unique combinatorial signatures directly into the structure of each HCR product. Sensitive quantitative amplification can be achieved using nonlinear HCR mechanisms that offer exponential growth into tethered polymers of a prescribed finite size. Finally, biocompatibility for in vivo applications follows from the use of nucleic acid amplifier components.

Definitions

"Nucleic Acids" as used herein means oligomers of DNA or RNA. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

The term "sticky end" refers to a nucleic acid sequence that is available to hybridize with a complementary nucleic acid sequence. The secondary structure of the "sticky end" is such that the sticky end is available to hybridize with a complementary nucleic acid under the appropriate reaction conditions without undergoing a conformational change. Typically the sticky end is a single stranded nucleic acid.

"Monomers" are individual nucleic acid oligomers. Typically, at least two monomers are used in hybridization chain reactions, although three, four, five, six or more monomers may be used. In some embodiments more than two monomers are utilized, such as in the HCR systems displaying quadratic and exponential growth discussed below. Typically each monomer comprises at least one region that is complementary to at least one other monomer being used for the HCR reaction.

A first monomer in a monomer pair preferably comprises an initiator complement region that is complementary to a portion of an initiator molecule. The initiator complement region is preferably a sticky end. Binding of the initiator to the initiator complement region begins an HCR reaction.

In addition, the second monomer preferably comprises a propagation region that is able to hybridize to the initiator complement region of another monomer, preferably another copy of the first monomer, to continue the HCR reaction begun by the initiator. The propagation region may be, for example, the loop region of a hairpin monomer as described below. In one embodiment the propagation region on the second monomer is identical to the portion of the initiator that is complementary to the initiator complement region of the first monomer.

The propagation region on the second monomer is preferably only available to interact with the initiator complement region of the first monomer when an HCR reaction has been started by the initiator. That is, the propagation region becomes available to hybridize to the initiator complement region of another monomer when one copy of the first monomer has already hybridized to a second monomer, as discussed in more detail below.

Preferred monomers are "metastable." That is, in the absence of an initiator they are kinetically disfavored from associating with other monomers comprising complementary regions. "HCR" monomers are monomers that are able to assemble upon exposure to an initiator nucleic acid to form a polymer.

As used herein, "polymerization" refers to the association of two or more monomers to form a polymer. The "polymer" may comprise covalent bonds, non-covalent bonds or both. For example, in some embodiments two species of monomers are able to hybridize in an alternating pattern to form a polymer comprising a nicked double helix. The polymers are also referred to herein as "HCR products."

An "initiator" is a molecule that is able to initiate the polymerization of monomers. Preferred initiators comprise a nucleic acid region that is complementary to the initiator complement region of an HCR monomer.

Monomers

Two or more distinct species of nucleic acid monomers are preferably utilized in an HCR reaction. Each monomer species typically comprises at least one region that is complementary to a portion of another monomer species. However, the monomers are designed such that they are kinetically trapped and the system is unable to equilibrate in the absence of an initiator molecule that can disrupt the secondary structure of one of the monomers. Thus, the monomers are unable to polymerize in the absence of the initiator. Introduction of an initiator species triggers a chain reaction of alternating kinetic escapes by the two or more monomer species resulting in formation of a polymer. In the examples below, the two hairpin monomers polymerize in the presence of an initiator to form a nicked, double helix.

In a preferred embodiment, two or more monomer species are employed that have a hairpin structure. The hairpin monomers preferably comprise loops protected by long stems. In other embodiments, monomers with a different secondary structure are provided. However, the secondary structure is preferably such that the monomers are metastable under the reaction conditions in the absence of an initiator nucleic acid. In the presence of an initiator, the secondary structure of a first monomer changes such that it is able to hybridize to a sticky end of a second monomer species. This in turn leads to a change in the secondary structure of the second monomer, which is then able to hybridize to another first monomer and continue the process. In this way, once a single copy of the first monomer interacts with a single copy of the initiator, a chain reaction is produced such that the monomers are able to assemble into a polymer comprising alternating monomer species.

A number of criteria can be used to design the monomers to achieve the desired properties. These include, for example and without limitation, sequence symmetry minimization, the probability of adopting the target secondary structure at equilibrium, the average number of incorrect nucleotides at equilibrium relative to the target structure, and hybridization kinetics.

Monomers can be synthesized using standard methods, including commercially available nucleic acid synthesizers or obtained from commercial sources such as Integrated DNA Technologies (Coralville, Iowa).

In some embodiments, monomers are derivitized with a compound or molecule to increase the molecular weight of the polymer resulting from HCR. Preferably they are derivitized at a location that does not interfere with their ability to hybridize. In other embodiments monomers comprise a fluorophore or colorimetric compound that allows the resulting polymers to be visualized.

In preferred embodiments, at least two hairpin monomers are utilized as illustrated in FIG. 1A. The monomers each preferably comprise a sticky end (a and c*, respectively), a first complementary segment (b and b*, respectively), a loop segment (c and a*, respectively), and a second complementary segment (b and b*, respectively). The first and second complementary segments are also referred to as "stems" and together form a duplex region.

Figure 1B:
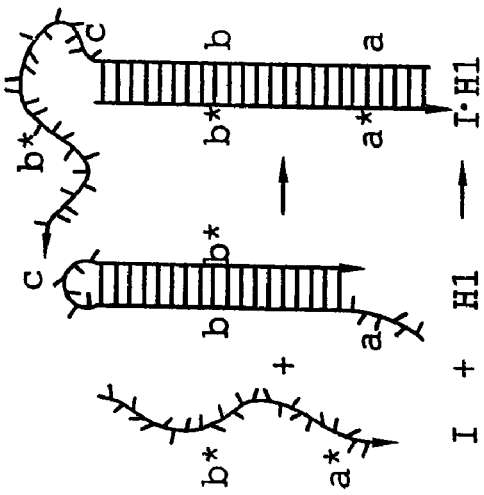
FIG. 1B shows how a single initiator strand 'I' can nucleate or bind to the sticky end of H1 and displace one arm to open the hairpin. This frees up the bases that were trapped in the hairpin, allowing them to perform a similar displacement reaction on H2.

The first monomer (H1) preferably comprises a sticky end a that is complementary to a first nucleic acid portion a* of an initiator (I; FIG. 1B). This sticky end is referred to herein as the "initiator complement region." The initiator may be, for example, an analyte of interest, or a nucleic acid that is able to contact the first monomer only in the presence of an analyte of interest, as discussed in more detail below.

The second monomer (H2) preferably comprises a sticky end c* that is complementary to a portion of the first monomer that becomes accessible upon initiator binding. Preferably the sticky end c* is complementary to the loop segment c of the first monomer (FIG. 1A). The loop segment c of the first monomer is preferably not available to hybridize with sticky end c* of the second monomer in the absence of initiator.

The first and second complementary segments (b and b*) in the first and second monomers are typically substantially identical. That is, the first complementary segment b of the first monomer (H1) is able to hybridize to the second complementary segment b* of the second monomer (H2).

The first complementary segment of each monomer is also able to hybridize to the second complementary segment of the same monomer to form the hairpin structure. For example, as shown in FIG. 1A, the first monomer (H1) comprises a first complementary segment b that is able to hybridize to the second complementary segment b*. In the absence of an initiator, the first and second complementary segments of each monomer are generally hybridized to form a duplex region of the metastable monomer.

Preferably, the first complementary segment b of the first monomer is also complementary to a portion b* of the initiator, such that upon hybridization of the initiator region a* to the sticky end a (the initiator complement region) of the first monomer H1, one arm of the hairpin structure is displaced. This opens the hairpin and allows binding of the first complementary segment b to the second portion b* of the initiator strand (FIG. 1B).

Figure 1C:
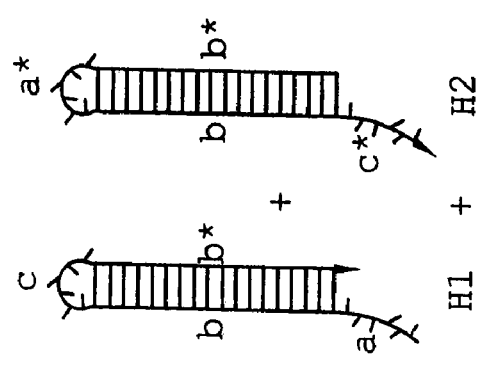
As illustrated in FIG. 1C, the newly exposed c region of H1 nucleates at the sticky end of H2 and opens the hairpin to expose a region on H2 (a*) that is identical in sequence to the initiator I. As a result, each copy of I can propagate a chain reaction of hybridization events between alternating H1 and H2 hairpins to form a nicked double helix, thereby amplifying the signal of initiator binding. The process can continue until the monomers (H1 and H2) are exhausted. At each step, energy is gained from the hybridization of 'a' or 'c'. The reactions diagrammed in FIG. 1 have been successfully carried out and are summarized in FIG. 1D.

The loop segment c of the first monomer is also exposed by the opening of the hairpin and is able to bind to the sticky end c* of the second monomer H2, as illustrated in FIG. 1C. This opens the second monomer hairpin H2 and the second complementary segment b* of the first monomer is able to hybridize to the first complementary segment b of the second monomer H2.

This leaves the loop region a* and first complementary region b* of the second monomer H2 exposed (FIG. 1C). The sticky end a of another first monomer (H1) species is able to bind to the exposed loop region a* of the second monomer H2, thus opening the H1 hairpin and continuing the process described above. Because the loop region a of the second monomer acts as an initiator on a second H1 monomer and allows the process to continue in the absence of further initiator, it is referred to as the propagation region.

At each step, energy is gained from the hybridization of the sticky end of the monomer. The result is a nicked, double helix polymer comprising alternating H1 and H2 fragments. This process preferably continues in a chain reaction until all of one or both of the monomer species is used up, or the reaction is stopped by some other mechanism. If desired, the nicks in the nucleic acid polymer structures that result from HCR can by ligated (for example, using T4 DNA ligase).

Because of the self-propagating nature of the reaction, each copy of the initiator species can begin the chain reaction. Further, as long as there is a fixed supply of monomers the average molecular weight of the resulting polymers is inversely related to the initiator concentration, as can be seen in FIG. 1D.

The length of the loop, stem and sticky ends of the monomers can be adjusted, for example to ensure kinetic stability in particular reaction conditions and to adjust the rate of polymerization in the presence of initiator. In one preferred embodiment the length of the sticky ends is the same as the length of the loops. In other embodiments the sticky ends are longer or shorter than the loops. However, if the loops are longer than the sticky ends, the loops preferably comprise a region that is complementary to the sticky end of a monomer.

In some preferred embodiments the length of the loops is short relative to the stems. For example, the stems may be two or three times as long as the loops.

The loop regions are preferably between about 1 and about 100 nucleotides, more preferably between about 3 and about 30 nucleotides and even more preferably between about 4 and about 7 nucleotides. In one embodiment the loops and sticky ends of a pair of hairpin monomers are about 6 nucleotides in length and the stems are about 18 nucleotides long.

Figure 6:
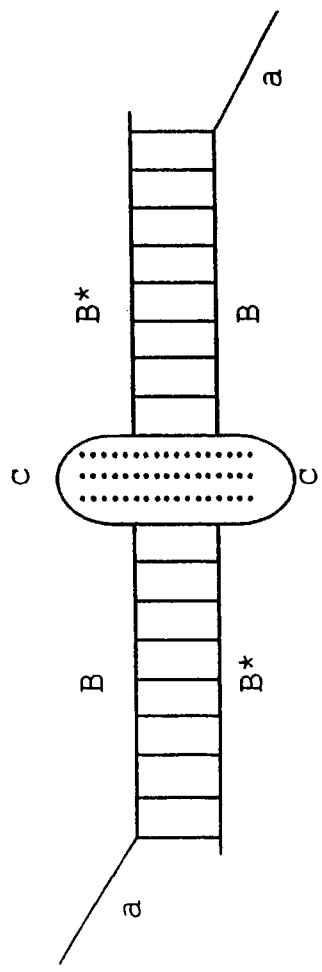
FIG. 6 illustrates a self-complementary hairpin with an interior loop that is a double helix (dotted lines). DNA hairpin can also exist as a dimer with an interior loop. One possible concern is that the interior loops may be easier to invade than the corresponding hairpins. To prevent this side reaction, self-complementary hairpins would convert the interior loop to a simple double helix (dotted lines). However, this added precaution may not be necessary.

Other refinements to the system stabilize the monomer hairpins to help prevent HCR in the absence of an initiator. This can be achieved, for example, via super-stable hairpin loop sequences (Nakano et al. Biochemistry 41:14281-14292 (2002)), with ostensible structural features that could further inhibit direct hybridization to the hairpin. In other embodiments hairpin loops are made to be self-complementary at their ends. This self-complementarity "pinches" the hairpin loops, making them shorter. However, if the reactive sticky ends of each monomer are complementary to the loop regions on the opposite monomer, as described above, they will have a slight propensity to close up, thereby slowing down the reaction. This feature can be utilized if a slower reaction is desired. Completely self-complementary hairpins can also be used, for example if the monomer hairpins are forming dimers with interior loops that are more easily invaded than their hairpin counterparts. FIG. 6 illustrates a self-complementary hairpin with an interior loop that is a double helix.

Reaction conditions are preferably selected such that hybridization is able to occur, both between the initiator and the sticky end of a first monomer, and between the complementary regions of the monomers themselves. The reaction temperature does not need to be changed to facilitate the hybridization chain reaction. That is, the HCR reactions are isothermic. They also do not require the presence of any enzymes.

Variations

There are many possible variations to HCR that may improve its speed, stability and ability to amplify chemical signals. The system illustrated in FIG. 1 and discussed above exhibits linear growth in response to initiator. However, increasing the rate of polymer growth can enhance the ability to detect the presence of low copy number targets, such as a single target molecule in a large test volume. For example, monomers can be designed to undergo triggered self-assembly into branched structures exhibiting quadratic growth or dendritic structures exhibiting exponential growth. The exponential growth is limited by the available space such that it decreases to cubic amplification as the volume around the initiator fills. However, if chain reactions products are able to dissociate, exponential growth can be maintained until the supply of monomers is exhausted.

In order to achieve non-linear growth, 3 or more HCR monomers can be used. In preferred embodiments at least 4 HCR monomers are used. In some embodiments, at least one monomer in a primary monomer pair incorporate a trigger nucleic acid segment that is complementary to the exposed sticky end of one of the monomers from a secondary set of HCR monomers. Upon exposure to the nucleic acid that is to be detected, the set of primary monomers undergoes HCR to form a polymer with a periodic single stranded trigger region. Thus the trigger nucleic acid is exposed, leading to a polymerization chain reaction in the secondary set of monomers. In other embodiments, both the primary and secondary set of monomers includes a trigger segment, such that exponential growth is achieved. Exemplary schemes are presented in FIGS. 2 and 3 for achieving quadratic and exponential growth, respectively.

In one embodiment, one of a first pair of monomers comprises a bulge loop. Upon polymerization, a single stranded region results from the presence of the bulge loop. The bulge loop segment is preferably complementary to the sticky end of one of a second pair of HCR monomers. Thus, upon exposure to the initiator, the first pair of monomers undergoes HCR to form a polymer with a single stranded region that acts to trigger polymerization of the second pair of monomers. FIGS. 2A-C depict such a quadratic amplification scheme. Monomers Q1 and Q2 interact with hairpin monomers H1 and H2 (FIG. 1) after initiation by $I_Q$ to form the branched polymer schematically illustrated in FIG. 2D.

Q1 and Q2 (FIG. 2a) are metastable in the absence of the initiator $I_Q$. $I_Q$ binds to Q1 and a subsequent strand displacement interaction exposes segments f, e* and b* as shown in FIG. 2B. This single-stranded region contacts sticky end f* of Q2 and a subsequent branch migration exposes segments c, b*, d* and e*. Segment d* then interacts with another copy of Q1 at sticky end d, causing the hairpin to open up such that e* can also hybridize. At the same time, the exposed c segment initiates a linear HCR reaction with hairpins H1 and H2 (not shown). The resulting branched polymer has a main chain comprising alternating Q1 and Q2 segments and H1/H2 side chains branching off at each Q2 segment.

In a further embodiment, exponential growth is achieved in response to an initiator by combining two or more pairs of monomers. For example, monomer pair Q1 and Q2 (FIG. 2) can be used in conjunction with monomers E1 and E2 (FIG. 3) to obtain exponential growth in response to an initiator. In the presence of nucleic acid segment cb*, E1 and E2 form a linear chain that includes periodic single stranded d*e* regions. By design, the initiator sequence for E1/E2 matches the periodic single stranded region produced by Q1/Q2 and vice versa. Consequently, a mixture of Q1, Q2, E1 and E2 monomers in the presence of initiator will form a structure in which each branch of the polymer is itself a branched polymer. Either initiator cb*, corresponding to the sticky end and first complementary region of E1, or d*e*, corresponding the sticky end and first complementary region of Q1, will activate the chain reaction.

While non-linear amplification systems provide enhanced sensitivity over a linear system, they may also have an increased chance for spurious initiation of HCR and a resultant increase in false-positive signals. Several methods may be used to decrease the possibility for initiation of the system in the absence of the initiator. In systems utilizing hairpin monomers, these may include helix clamping, helix elongation and loop entropy ratchets.

Figure 3:
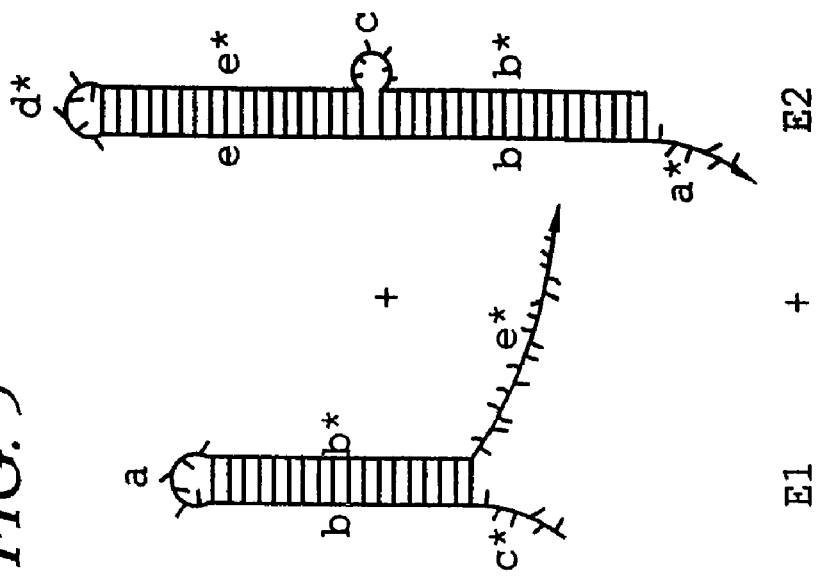
FIG. 3 illustrates a pair of monomers (E1 and E2) that can be used in combination with at least one other pairs of monomers to achieve exponential amplification by HCR. In the presence of cb*, E1 and E2 form a linear chain that includes periodic single stranded d*e* regions. The initiator sequence for E1/E2 matches the periodic single stranded region produced by Q1/Q2 and vice versa. Consequently, a mixture of Q1, Q2, E1 and E2 plus either initiator (cb* or d*e*) will lead to the formation of a structure in which each branch of the polymer is itself a branched polymer. Sustained growth will ultimately decrease to cubic amplification.

The quadratic and exponential growth HCR schemes illustrated in FIGS. 2 and 3 include long single-stranded regions (b* and e* respectively). These long regions could potentially function as weak initiators. Several methods are available to reduce spurious monomer polymerization in the absence of initiator for both higher order growth schemes and linear growth schemes. These include helix clamping, helix lengthening and loop entropy ratchets. In helix clamping, the single stranded regions in one or more of the monomers are truncated at each end so that the helixes that they could potentially invade in other monomers are effectively clamped at the ends by bases that are not present in the single stranded (b* and e*) regions. Experiments have shown that this can eliminate any spurious initiation. The amount of truncation that is effective to decrease or eliminate spurious initiation can be determined by routine experimentation. For example, control experiments can be performed using fluorescent gel electrophoresis time courses to monitor strand exchange between single stranded DNA and duplex DNA (e.g., strand b* invading duplex bb*) for different clamp lengths. Using spectrally distinct dyes for the initially single stranded DNA and for the two DNA species in the duplex allows independent monitoring of all species as strand exchange proceeds. These controls can provide a systematic basis for section of clamp dimensions.

The length of the helices in the linear HCR scheme illustrated in FIG. 1 contributes directly to the height of the kinetic barrier that prevents spurious polymerization between the two hairpin species. Interactions between H1 and H2 are sterically impeded by the loop size. However, the long helices (bb*) in each hairpin provide a more fundamental kinetic barrier; the length of the helices has a direct effect on the height of the kinetic barrier that impedes spurious HCR. An increase in the length of the helices will increase the initial kinetic barrier in the uninitiated system. Thus, in some embodiments utilizing hairpin monomers, for example if spurious initiation is observed, the length of the duplex region can be increased to reduce the background noise. The helix length necessary to reduce polymerization in the absence of initiator to an acceptable level can be readily determined by routine experimentation. In some embodiments helix lengthening is combined with helix clamping.

In still other embodiments utilizing hairpin monomers, loop entropy ratchets are used to reduce HCR in the absence of initiator. An initiator opens an HCR hairpin via a three-way branch migration. This reaction is reversible because the displaced strand is tethered in the proximity of the new helix. However, by increasing the length of the single-stranded loop, the entropy penalty associated with closing the loop increases. As a result, a longer loop will bias the reaction to proceed forward rather than returning to the uninitiated state. However, larger loops are more susceptible to strand invasion. To counter this effect and allow the use of larger loops, mismatches can be introduced between the loop sequences and the complementary regions of the other monomers. Again, the loop length and amount of mismatch that produces the desired reduction in non-specific HCR can be determined by the skilled artisan through routine experimentation.

Initiator

The initiator is preferably a nucleic acid molecule. The initiator comprises an initiator region that is complementary to a portion of an HCR monomer, preferably a portion of the monomer that is available for hybridization with the initiator while the monomer is in its kinetically stable state. The initiator also preferably comprises a sequence that is complementary to a portion of the monomer adjacent to the sticky end such that hybridization of the initiator to the sticky end causes a conformational change in the monomer and begins the HCR chain reaction. For example, the initiator may comprise a region that is complementary to the first complementary region of the HCR monomer, as described above.

In the preferred embodiments, the sequence of the initiator is complementary the sticky end (initiator complementary region) and first complementary region of a first monomer. As described above, in some embodiments this will also influence the sequence of the second complementary region and the loop of the second monomer species.

In some embodiments the initiator is a nucleic acid that is to be detected in a sample or a portion of a nucleic acid that is to be detected. In this case, the sequence of the target nucleic acid is taken into consideration in designing the HCR monomers. For example, the initiator complement region, preferably a sticky end, of one monomer is designed to be complementary to a portion of the target nucleic acid sequence. Similarly, a region adjacent to the sticky end of the same monomer can be designed to be complementary to a second region of the target sequence as well. Because the second monomer will hybridize to the first monomer, the sequence of the second monomer will also reflect at least a portion of the sequence of the target nucleic acid.

In other embodiments, the initiator comprises at least a portion of a nucleic acid that is part of a "initiation trigger" such that the initiator is made available when a predetermined physical event occurs. In the preferred embodiments that predetermined event is the presence of an analyte of interest. However, in other embodiments the predetermined event may be any physical process that exposes the initiator. For example, and without limitation, the initiator may be exposed as a result of a change in temperature, pH, the magnetic field, or conductivity. In each of these embodiments the initiator is preferably associated with a molecule that is responsive to the physical process. Thus, the initiator and the associated molecule together form the initiation trigger. For example, the initiator may be associated with a molecule that undergoes a conformational change in response to the physical process. The conformational change would expose the initiator and thereby stimulate polymerization of the HCR monomers. In other embodiments, however, the initiation trigger comprises a single nucleic acid. The initiator region of the nucleic acid is made available in response to a physical change. For example, the conformation of the initiation trigger may change in response to pH to expose the initiator region.

The structure of the trigger is preferably such that when the analyte of interest is not present (or the other physical event has not occurred), the initiator is not available to hybridize with the sticky end of a monomer. Analyte frees the initiator such that it can interact with a metastable monomer, triggering the HCR polymerization reactions described above. In some embodiments analyte causes a conformational change in the trigger that allows the initiator to interact with the monomer.

The initiator may be part of a trigger comprising a nucleic acid that is linked to or associated with a recognition molecule, such as an aptamer, that is capable of interacting with an analyte of interest. The trigger is designed such that when the analyte of interest interacts with the recognition molecule, the initiator is able to stimulate HCR. Preferably, the recognition molecule is one that is capable of binding the analyte of interest.

Recognition molecules include, without limitation, polypeptides, such as antibodies and antibody fragments, nucleic acids, such as aptamers, and small molecules. The use of an initiator bound to an aptamer is described in more detail below.

In some particular embodiments, amplification of diverse recognition events is achieved by coupling HCR to nucleic acid aptamer triggers. An aptamer is identified that is able to specifically bind an analyte of interest. The analyte is not limited to a nucleic acid but may be, for example, a polypeptide or small molecule. The aptamer is linked to a nucleic acid comprising an initiator region in such a way that the initiator is unavailable to stimulate HCR in the absence of analyte binding to the aptamer.

Preferably, conformational changes in the aptamer secondary structure expose the initiator segment. In one embodiment, such an aptamer trigger is a hairpin nucleic acid that comprises an initiator segment that is complementary to the initiator complement region or sticky end of an HCR monomer. The aptamer trigger also comprises a complementary region that is complementary to a region of the HCR monomer adjacent to the sticky end, a loop region and an aptamer sequence. The hairpin aptamer trigger may also comprise a region that enhances the stability of the hairpin in the absence of aptamer binding to the analyte, such as a nucleic acid region in one arm of the hairpin that is complementary to a region of the other arm.

Figure 5B:
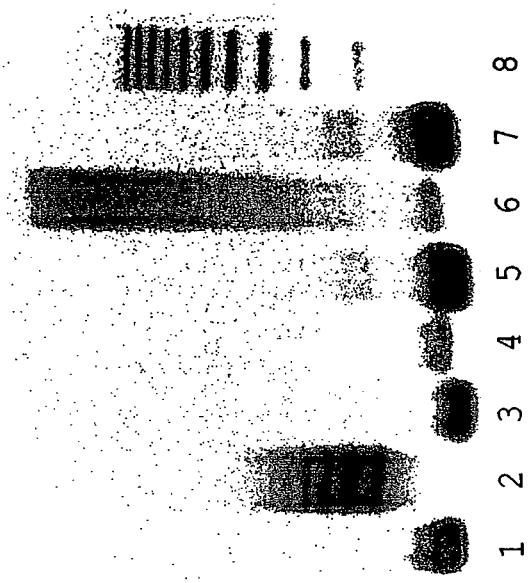
FIG. 5B shows an agarose gel demonstrating ATP detection via HCR.
Figure 5A:
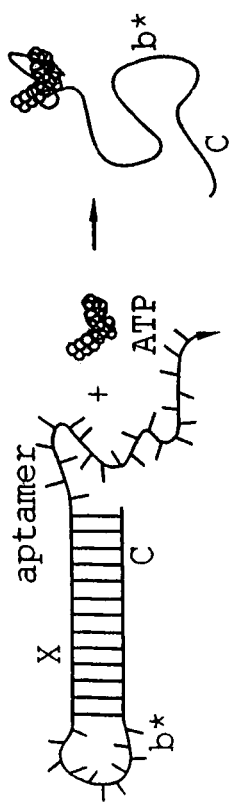
FIG. 5A illustrates an aptamer HCR trigger mechanism for the detection of ATP. Binding of the DNA aptamer to ATP induces a conformation change that exposes a sticky end.

FIG. 5A depicts a scheme for HCR amplification of ATP binding using an aptamer construct that exposes an initiator strand upon ATP binding. The sticky end can act as a trigger for the HCR mechanism of FIG. 1 by opening hairpin H2. The region x is introduced to help stabilize the trigger in the absence of analyte. The region b* includes both the hairpin loop and the portion of the stem complementary to x. This trigger mechanism is based on conformational changes in the aptamer secondary structure (Yingfu Li (2003) Journal of the American Chemical Society 125:4771-4778) that make the initiator strand available to stimulate HCR. FIG. 5B illustrates successful detection of ATP, as well as specificity in differentiating ATP from GTP, as discussed in more detail in the Examples below.

Detecting HCR

The products of HCR are readily detectable by methods known to one of skill in the art for the detection of nucleic acids, including, for example, agarose gel electrophoresis, polyacrylamide gel electrophoresis, capillary electrophoresis, and gel-filled capillary electrophoresis. As the polymers comprise nucleic acids, they can be visualized by standard techniques, such as staining with ethidium bromide. Other methods also may be suitable including light scattering spectroscopy, such as dynamic light scattering (DLS), viscosity measurement, colorimetric systems and fluorescence spectroscopy. As discussed in more detail below, in the preferred methods for in situ imaging and detection, HCR products are fluorescently labeled.

In some embodiments HCR is monitored by fluorescence resonance energy transfer (FRET). Certain monomers are labeled with fluorescent dyes so that conformational changes resulting from HCR can be monitored by detecting changes in fluorescence. In one embodiment, one of a pair of hairpin molecules is labeled with a fluorophore at the junction of the region complementary to the initiator strand and the duplex region and labeled at the opposing side of the duplex region with a quencher molecule. Upon polymerization, the fluorophore and quencher are separated spatially in the aggregated nucleic acid structure, providing relief of the fluorescence quenching. In this case, the presence of a single initiator is amplified by the chain of fluorescent events caused by HCR. In the context of in situ imaging, the presence of a single target molecule can be amplified by the chain of fluorescence events. In addition, for in situ imaging the quenching of fluorescence in unreacted monomers reduces background noise. Thus, unreacted monomers do not need to be removed from the sample.

Because the size of the HCR products is inversely related to the amount of the target analyte in a sample, HCR can be used to determine analyte concentration. The average molecular weight of the HCR products is obtained by standard measurements. Is some embodiments the average molecular weight of HCR products obtained from one sample is compared to the average molecular weight of HCR products from one or more other samples with an unknown analyte concentration. In this way, the relative concentration of analyte in each sample can be determined.

In other embodiments, the concentration of analyte is determined by comparing the average molecular weight from a sample with unknown concentration to the average molecular weight of HCR products from HCR reactions in one or more control samples with a known concentration of the analyte. In this way the concentration of analyte in the unknown samples can be determined to be the same as one of the control samples, greater than one of the control samples, less than one of the control samples, or in the rance of concentration between two control samples. Thus, the number of control reactions can be adjusted based on the particular circumstances to provide more or less sensitive determination of analyte concentration. For example, if a relatively exact analyte concentration is necessary, the number of control samples can be increased. On the other hand, if only a broad idea of analyte concentration is necessary, fewer control samples can be used.

Application to In situ Imaging

HCR provides an enzyme-free approach to in situ amplification that can be multiplexed in parallel. Furthermore, HCR amplification provides a means for reducing the background signal resulting from nonspecific probe binding. Probes for the target to be detected in a biological sample incorporate an HCR initiator. After binding to the target, the initiator triggers the self-assembly of tethered (to the target) non-covalent 'polymers' built from HCR monomers, preferably hairpin monomers as described above. The HCR monomers are preferably fluorescently labeled so that the polymers can be detected and the presence and/or location of the target determined.

Figure 9:
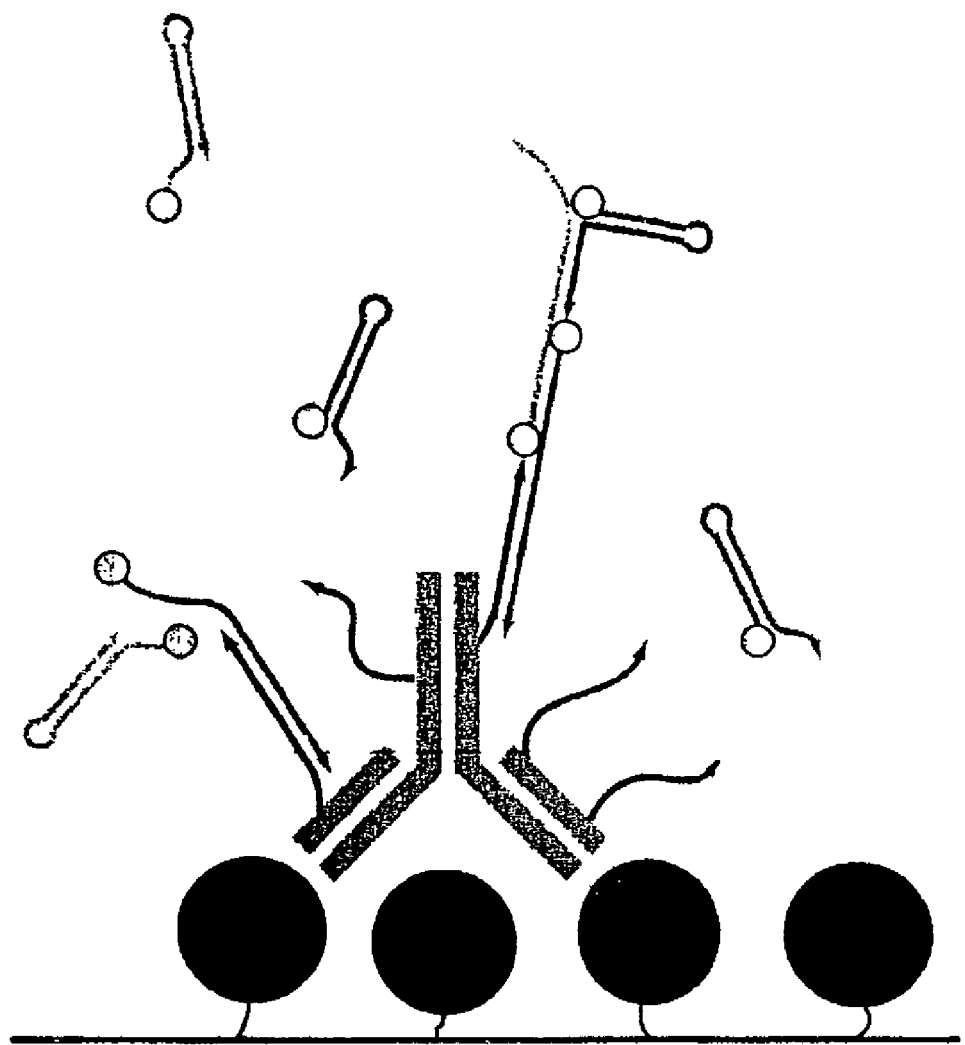
FIG. 9 illustrates an HCR antibody probe.

In addition to an initiator, probes also preferably comprise a target region that is able to specifically bind to or associate with a target. In some embodiments, particularly where the target is a nucleic acid, such as a gene or mRNA, the probe target region comprises a nucleic acid. In other embodiments the probe target region comprises a polypeptide, such as an antibody (FIG. 9).

The HCR monomers are also referred to herein as "amplifiers" because the polymerization of the monomers upon binding of a probe to the target produces a detectable signal, which is amplified compared to the signal that would be produced by the binding of a single probe to the target. The amplifiers can each be labeled with the same or different fluorophores. For example, the system can be designed to use more than two monomer species per target, with at least one species fluorescently labeled. Fluorescent labels are well known to one of skill in the art and include those, for example, in the "The Handbook—A Guide to Fluorescent Probes and Labeling Technologies," 10th Edition (available at http://www.probes.com).

In some embodiments, amplifiers within the system are labeled with both a fluorophore and a quencher to form a construct analogous to a "molecular beacon" (Tyagi et al. Nature Biotechnology 14:303-308, 1996). For example, a hairpin monomer can comprise both a fluorophore and a quencher, such that the quencher reduces fluorescence while the monomer is in the hairpin form but not when the monomer is incorporated into an HCR polymer. Thus, molecular beacon versions of HCR monomers can reduce background signal resulting from any unpolymerized monomers, such as those that bind non-specifically or that simply remain unreacted in the sample.

For imaging of biological samples, it is advantageous to use amplifier components that are small in size to allow penetration into the sample. For example, in some embodiments HCR components less than about 20 nanometers are used. More preferably the HCR components are less than about 15 nm, even more preferably less than about 10 nm, and still more preferably between about 8 and 16 nm. In some particular embodiments the HCR monomers are less than about 8 nm. Standard procedures for in situ imaging can be used to cause the HCR products to enter the sample. The skilled artisan will be able to select the appropriate methods for causing the HCR components to enter the sample.

Figure 8:
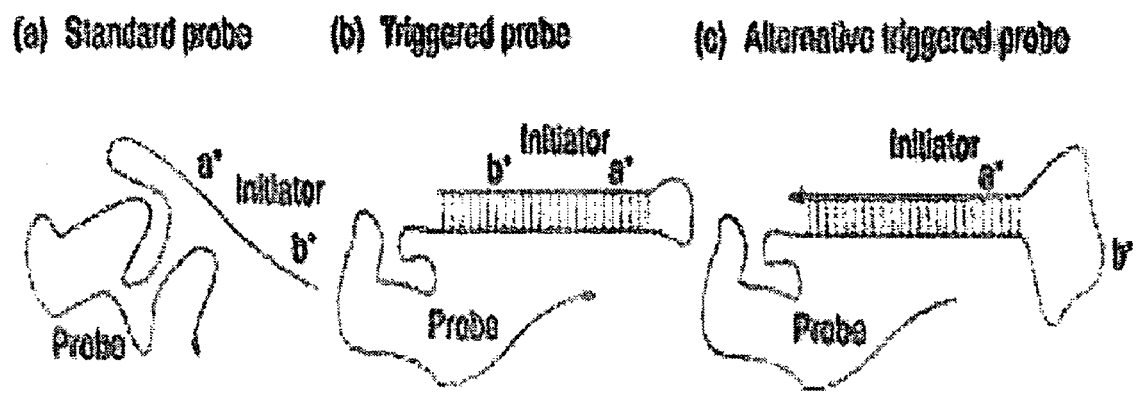
FIG. 8 is a schematic illustration of HCR probes for in situ HCR amplification. A standard probe illustrated in FIG. 8A leaves the HCR initiator exposed at all times. A triggered probe (FIG. 8B) protects the initiator until specific binding of the probe to the target mRNA exposes the initiator. An alternative triggered probe (FIG. 8C) reduces the sequence dependence of the amplifier hairpins on the target mRNA (sequence b* is now independent of the target sequence).

Active Background Suppression Using Triggered Probes and Self-quenching Components For in situ hybridization studies, the simplest probe design incorporates an initiator strand at the end of the probe molecule (FIG. 8A). The probe portion of the probe is specific for the target molecule that is to be detected in the sample. For example, the probe portion can comprise a nucleic acid that is complementary to a portion of a gene of interest or to an mRNA of interest. In another embodiment the probe comprises a protein or nucleic acid, such as an aptamer, that is able to bind to or associate with the target. For example, the probe may comprise an antibody, antibody fragment, DNA binding protein or other nucleic acid or polypeptide that is able to bind a target of interest. In one embodiment, illustrated in FIG. 9, the probe comprises an antibody that is specific for a protein of interest coupled to an initiator.

After performing probe hybridization (or binding) and washing the sample to remove unbound probes, HCR hairpins can be introduced. The presence of the initiator portion of the probe causes the HCR hairpins (or amplifiers) to self-assemble "polymers," essentially as described above for general HCR. However, in this context, the polymers will remain tethered to the target, such as an mRNA. In some preferred embodiments the amplifiers are fluorescently labeled, such that the resulting polymers have about 8 nm dye spacing.

If the probe of FIG. 8A binds nonspecifically in the sample, then the initiator will cause HCR amplification at a location where no target was detected. All fluorescent in situ hybridization methods currently suffer from the problem of background signal resulting from nonspecific probe binding. However, with HCR amplification it is possible to avoid excessive non-specific background with the use of a triggered probe.

Using HCR amplification, it is conceptually straightforward to design "triggered probes" that actively suppress background from nonspecific binding, particularly when the target molecule is a nucleic acid. One such probe is illustrated in FIG. 8B. With a triggered probe, specific probe binding to a nucleic acid target exposes the initiator strand via a strand displacement interaction. The initiator is then kinetically impeded from returning to its protected state by the base pairs formed between the target and the previously looped portion of the probe (the strength of this free energy ratchet can be adjusted by changing the size of the loop). However, if nonspecific probe binding occurs, the initiator remains protected and HCR amplification is prevented.

The triggered probe design of FIG. 8B implies that subsequences a and b of the HCR amplifier hairpins are constrained to be within a window of consecutive bases from a target mRNA (a=6 bases, b=18 bases for the standard HCR hairpin design). If desirable, the dependence of the amplifier hairpins on the target sequence can be reduced using the design of FIG. 8C, in which only subsequence "a" is determined by the target mRNA sequence. This change dramatically increases the flexibility in designing multiple orthogonal amplifier systems. If it becomes desirable to eliminate the sequence dependence completely, this can also be accomplished using an additional branch migration step (not shown).

In other embodiments, the triggered probe is configured such that a change in conformation upon target binding releases an initiator strand or otherwise makes the initiator region available to interact with an HCR monomer to initiate polymerization. Such probes can be used, for example, to detect nucleic acids, but also to detect targets that are not nucleic acids, such as polypeptides.

Once a triggered probe has been activated by binding (or associating) specifically to a target, fluorescently labeled HCR monomers, preferably hairpins, can self-assemble into a tethered amplification polymer. Because the initiator is protected prior to target binding, it is not necessary to remove unbound probe prior to providing HCR monomers to the system. Thus, HCR monomers can be provided to the system at the same time as the triggered probe. However, in some embodiments unbound probe is washed prior to providing the HCR monomers.

Figure 10:
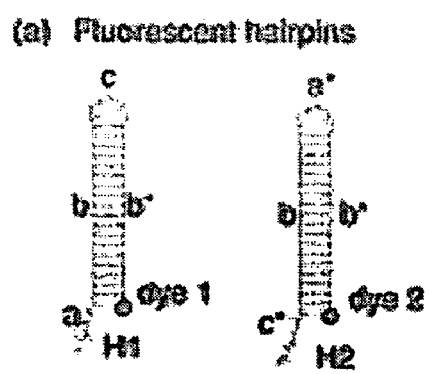
FIG. 10 schematically illustrates fluorescent labeling schemes for in situ HCR amplification.
Figure 10:
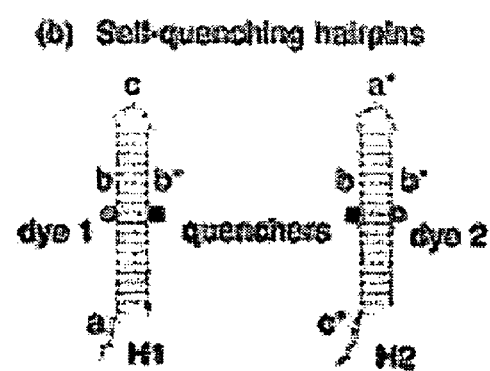
Figure 10:
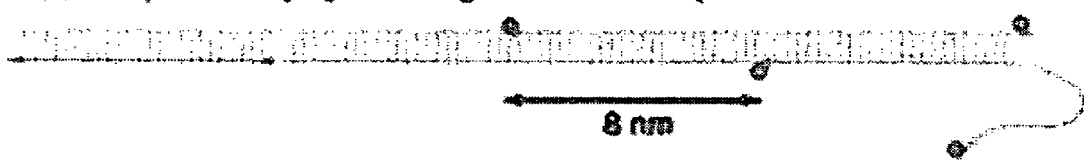
Figure 10:
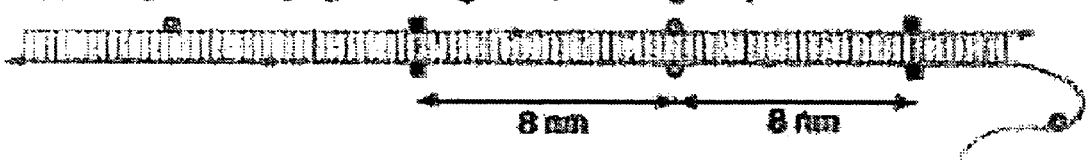

FIGS. 10A and 10C illustrate standard end-labeled hairpins (FIG. 10A) and the corresponding amplification polymer (FIG. 10C) with dyes placed at about 8 nm spacing. For some samples, such as fixed whole mount samples, unused labeled monomers can be washed from the sample to reduce background signal. However, this approach is not suitable for all samples and all applications. For example, it is not viable for in vivo imaging. Thus, in some embodiments active background suppression can instead be achieved by making the HCR hairpins self-quenching using fluorophore/quencher pairs (FIG. 10B). In the hairpin form (FIG. 10B), fluorophore/quencher pairs have about 2 nm spacing, but the hairpins are labeled so that each fluorophore is about 8 nm from the nearest quenchers after amplification occurs (FIG. 10D). After polymerization, the neighboring dyes will have about 2 nm separation. Within a given polymer, the dyes can be chosen to be identical (a single-color amplifier) or to have non-overlapping excitation and emissions spectra.

Figure 11:
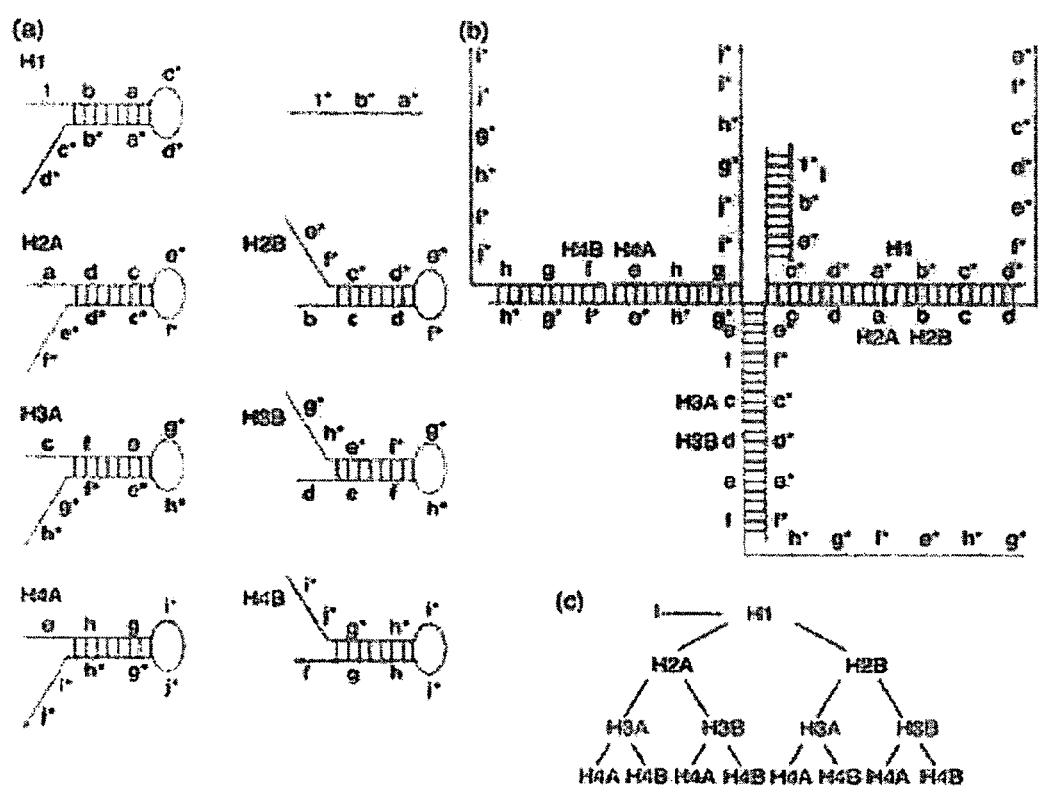
FIG. 11 illustrates a scheme for quantitative nonlinear HCR amplification.

Quantitative Amplification Via Triggered Self-assembly of Fixed-size Amplification Polymers To increase the sensitivity of HCR schemes while achieving a fixed level of amplification per target molecule to provide quantitative signal strength, branched nonlinear amplification schemes that form polymers of a pre-defined size can be used (FIG. 11). Amplification components are shown in FIG. 11A. The amplification polymer branches to form a binary tree (FIG. 11B) using two HCR monomer species for each generation of branching (FIG. 11C).

In the absence of steric effects, the polymer will grow exponentially to a prescribed size determined by the number of hairpin generations that are in solution. If each hairpin is labeled with F fluorophores, a tree with G generations requires 2G−1 hairpins and yields $F(2^G-1)$ dyes tethered to the triggered probe. Only the first two generations (comprising hairpins H1, H2A, and H2B) are related to the probe sequence, so subsequent generations can be used as standardized amplifier components. Hence, after designing and synthesizing components for M orthogonal amplification trees, the components can be re-used for simultaneous multiplexing of any M targets of interest. For active background suppression in vivo, self-quenching hairpins can be obtained by again using fluorophore/quencher pairs.

In an analogous fashion to the self-quenching scheme of FIGS. 10B and 10D, the labels can be arranged so that quenchers are clustered away from the fluorophores in the assembled polymer. After some number of generations, exponential growth must slow to cubic growth as the volume around the initiator fills. To increase the number of generations of exponential growth, spacer regions can be introduced into the hairpins to increase the separation between clusters of the same generation.

Imaging Multiple Analytes

A major conceptual benefit of HCR amplification is the ability to amplify multiple targets simultaneously. HCR targeting a number of analytes (for example, gene transcripts or proteins) can be used simultaneously. In one embodiment, each HCR system is labeled with a spectrally distinguishable dye. Accordingly, the number of analytes is equal to the number of spectrally distinguishable dyes that are available. For many situations, this will be sufficient.

To study the expression of multiple mRNAs or proteins, it is desirable to perform multiplexed amplification of all recognition events simultaneously using orthogonal HCR amplifiers. To maximize the number of distinct targets that can be imaged using a limited supply of spectrally distinct fluorophores, the unamplified combinatorial multiplexing approach of Levsky and co-workers (Levsky et al. Science 297:836-840, 2002) can be adapted for HCR amplification by labeling the monomers for each amplifier with different unique dye combinations The use of barcodes with a minimum of two colors provides a basis for screening single-color signals resulting from probes that are not bound specifically. However, triggered probes for HCR amplification already have a built-in capability to reduce background.

Therefore, in some embodiments only a single probe is used for each target and combinatorial multiplexing is performed by labeling the monomers for each HCR amplifier with different unique dye combinations. This approach is preferable to a combinatorial approach in which you just make a probe for a target that you then independently amplify with two one-color systems. Firstly, that method doesn't work for single-molecule detection, and second, there is no guarantee on the relative ratio of each dye that would be deposited in that case.

If the H1 and H2 hairpins are end-labeled with different dyes, the HCR product will carry an equal number of each dye by construction. In general, N spectrally distinct fluorophores can be used to address T: $N!/[(N-2)!2!]$ targets with dual-color amplifiers (e.g., 4 dyes for 6 targets, 5 dyes for 10 targets). However, since combinatorial barcodes are not employed as a background diagnostic using this approach, the number of targets can be increased to $T=N![N-2]!2!+N$ by allowing single-color amplifiers (e.g., 4 dyes for 10 targets, 5 dyes for 15 targets). Furthermore, it is possible to label HCR monomers with more than one dye to increase the number of targets that can be addressed up to $T=\Sigma_{(i=1,N)}N!/[(N-i)!i!]=2^N-1$ (e.g., 4 dyes for 15 targets, 5 dyes for 31 targets). HCR systems also can be designed that used M hairpins per amplifier.

Figure 7:
FIG. 7 is a picture of a gel showing independent operation of two HCR systems in the same solution. System 1 comprised hairpins H1A and H1B and initiator I1. System 2 comprised hairpins H2A and H2B and initiator I2. Hairpins H1B and H2B were 5'-labeled with fluorophores FAM (red signal) and Cy3 (green signal), respectively. All reactions contained all four hairpin species at 0.5 μM. Lane 1: No reaction was seen in the absence of initiators. Lanes 2 and 3: specific detection of I1 (1× and 0.25×, respectively). Lanes 4 and 5: specific detection of I2 (1× and 0.25×, respectively). Lanes 6 and 7: simultaneous detection of I1 and I2 (1× and 0.25×, respectively).

As a proof of principle, FIG. 7 demonstrates simultaneous and specific detection of two different DNA fragments using two HCR amplification systems.

EXAMPLES

HCR monomers comprising DNA sequences were designed using a combination of criteria (Dirks et al. Nucleic Acids Research 32:1392-1403 (2004)). These included sequence symmetry minimization (Seeman N. C. J. Theor. Biol. 99:237-247 (1982)), the probability of adopting the target secondary structure at equilibrium (Hofacker et al. Monatsh. Chem. 125:167-188 (1994)), the average number of incorrect nucleotides at equilibrium relative to the target structure (Dirks et al. Nucleic Acids Research 32:1392-1403 (2004)) and hybridization kinetics (Flamm et al. RNA 6:325-338 (2000)). The sequences of the monomers and initiator for the basic HCR system illustrated in FIG. 1 and the aptamer trigger HCR system illustrated in FIG. 5 are shown in Table 1. The aptamer system included new sequences to ensure compatibility with the fixed sequence of the aptamer. DNA was synthesized and purified by Integrated DNA Technologies (Coralville, Iowa).

TABLE 1

| System | Strand | Sequence* |
|--------|--------|-----------|
| Basic | H1 | 5'-*TTA ACC* CAC GCC GAA TCC TAG ACT CAA AGT AGT CTA GGA TTC GGC GTG-3' (SEQ ID NO: 1) |
|  | H2 | 5'-AGT CTA GGA TTC GGC GTG GGT TAA CAC GCC GAA TCC TAG ACT *ACT TTG*-3' (SEQ ID NO:2) |
|  | I | 5'-AGT CTA GGA TTC GGC GTG GGT TAA-3' (SEQ ID NO: 3) |
| Aptamer† | H1 | 5'-*CAT CTC* GGT TTG GCT TTC TTG TTA CCC AGG TAA CAA GAA AGC CAA ACC-3' (SEQ ID NO: 4) |
|  | H2 | 5'-*TAA* CAA GAA AGC CAA ACC GAG ATG GGT TTG GCT TTC TTG TTA *CCT GGG*-3' (SEQ ID NO: 5) |
|  | $I^{ATP}$ | 5'-CCC AGG TAA CAA GAA AGC CAA ACC TCT TGT TAC CTG GGG GAG TAT TGC GGA GGA AGG T-3' (SEQ ID NO: 6) |
|  | I | 5'-CCC AGG TAA CAA GAA AGC CAA ACC-3' (SEQ ID NO: 7) |

*In the hairpin sequences, loops are in bold and sticky ends are italicized.
†Aptamer nucleotides are italicized and bolded.

For the basic HCR system illustrated in FIG. 1, concentrated DNA stock solutions were prepared in buffer that was later diluted to reaction conditions. The buffer comprised 50 mM Na2HPO4/0.5M NaCl (pH 6.8).

Monomers H1 and H2 (FIG. 1B) were mixed at various concentrations in the presence and absence of initiator. Stock solutions of I, H1 and H2 were diluted in reaction buffer to three times their final concentration and 9 μl of each species was combined, in that order to give a 27 μl reaction volume. Six different concentrations of initiator were used (0.00, 10.00, 3.20, 1.00, 0.32 and 0.10 μM) in a 1 μM mixture of H1 and H2. Reactions were incubated at room temperature for 24 hours before running 24 μl of each product on a gel. Samples were loaded on 1% agarose gels containing 0.5 μg EtBr per ml of gel volume. The gels were prepared using 1× SB buffer (10 mM NaOH, pH adjusted to 8.5 with boric acid). The agarose gels were run at 150 V for 60 minutes and visualized under UV light.

FIG. 1D illustrates the results of the HCR reactions and the effect of initiator concentration on amplification. Lanes 2-7 of the gel shown in FIG. 1D are the results of the HCR reactions at the various initiator concentrations, respectively. Lanes 1 and 8 are DNA markers with 100-bp and 500-bp increments respectively. As illustrated by FIG. 1D, introduction of an initiator strand triggers a chain reaction of hybridization that results in the production of polymers of various sizes. The average molecular weight of the polymers is inversely related to the initiator concentration (FIG. 1(d)). The inverse relationship follows from the fixed supply of monomer hairpins, but the phenomenon was observed after 10 minutes, when the supply of monomers had not been exhausted.

These results confirmed an earlier experiment in which 1 μM of H1 and H2 were reacted overnight in 0.5M NaCl, 50 mM Na$_2$HPO$_4$ at pH 6.5 with initiator at concentrations of 0, 1, 0.1, 0.01, 0.001 and 0.0001 μM. With no initiator HCR reactions were not observed. In addition, no visible polymer growth was observed at initiator concentrations of 0.001 and 0.0001 μM. At the other initiator concentrations an inverse relationship was observed between the initiator concentration and the average molecular weight of the resulting polymers.

In another set of experiments, the aptamer trigger illustrated in FIG. 5A was utilized. The aptamer trigger ($I^{ATP}$) comprised an initiator region corresponding to the initiator used in the experiments described above, linked to an aptamer that is able to specifically interact with ATP (Huizenga et al. Biochemistry 34:656-665. (1995)). In addition, the aptamer trigger comprises a stabilizing region designed to stabilize the trigger in the absence of ATP. The aptamer trigger is designed such that in the presence of ATP the hairpin is opened and the initiator region exposed, thereby triggering polymerization of the H1 and H2 monomers. The sequence of $I^{ATP}$ is provided in Table 1, above.

Reactions were carried out with various combinations of H1, H2, I, $I^{ATP}$, ATP and GTP. Concentrated stock solutions of the constituents were diluted to reaction conditions: 5 mM MgCl2/0.3 M NaCl/20 mM Tris (pH 7.6). Reactions were performed with 1.4 mM ATP and/or GTP. DNA species were combined to yield 1 μM concentrations in 27 μl of reaction buffer, with additions made in the following order: buffer and/or initiator I or aptamer trigger $I^{ATP}$, H1, and then H2 (I and $I^{ATP}$ interact with H2 rather than H1). In this case, 1 μl of 40 mM ATP, 40 mM GTP or water was added to each reaction, as appropriate, for a total reaction volume of 28 μl.

Reactions were incubated at room temperature for one hour and run on agarose gels (as described above) or native polyacrylamide gels. Native polyacrylamide gels were 10% precast gels made with 1× TBE buffer (90 mM Tris, 89 mM boric acid, 2.0 mM EDTA, pH 8.0). The polyacrylamide gels were run at 150V for 40 minutes in 1× TBE and stained for 30 minutes in a solution containing 5 μg EtBr per ml.

FIG. 5B shows a representative agarose gel illustrating that the aptamer trigger $I^{ATP}$ can initiate polymerization of H1 and H2 in the presence of ATP and that ATP can be distinguished from GTP. Hairpins H1 and H2 did not polymerize when mixed in the absence of initiator (H1+H2; Lane 1), but did polymerize when the initiator I was added (H1+H2+I; Lane 2). ATP alone was unable to trigger the polymerization of the hairpin monomers (H1+H2+ATP; Lane 3) and no polymers were observed from the combination of aptamer trigger with ATP in the absence of hairpin monomers ($I^{ATP}$+ATP; Lane 4). Some weak spurious HCR was observed in the absence of ATP from the combination of monomers and aptamer trigger (H1+H2+$I^{ATP}$; Lanes 5) or in the presence of GTP (H1+H2+ $I^{ATP}$+GTP; Lane 7), respectively. Strong HCR amplification of ATP recognition was seen when the monomers were combined with the aptamer trigger in the presence of ATP (H1+ H2+$I^{ATP}$+ATP; Lane 6). A DNA ladder is shown in Lane 8 (100-1000 bp in 100 bp increments).

The kinetics of HCR reactions were explored using fluorescence quenching. The adenine analog 2-aminopurine (2AP) fluoresces when single stranded but is significantly quenched when in a stacked double-helical conformation (Rachofsky et al. Biochemistry 40: 996-956 (2001)). Monomer usage was monitored as polymerization occurred by replacing H1 with the labeled hairpin $H1^{2AP}$. $H1^{2AP}$ was prepared by substituting 2AP for the third base (A) in the sticky end of H1 (see Table 1). Monitoring 2AP fluorescence was used rather than standard end-labeled strands because the local environment of quenched 2AP was the same regardless of whether initiator (I) or monomer (H2) performs the quenching.

Fluorescence data were obtained using a fluorometer from Photon Technology International (Lawrenceville, N.J.), with the temperature controller set to 22° C. Excitation and emission wavelengths were 303 and 365 nm, respectively, with 4 nm bandwidths. Stock solutions of 0.40 μM H12AP and 0.48 μM H2 were prepared in reaction buffer as described above, heated to 90° C. for 90 seconds and allowed to cool to room temperature for 1 hour before use. For each experiment, 250 μl of H12AP was added to either 250 μl of H2 or 250 μl of reaction buffer. These 0.20 μM H12AP solutions were allowed to sit at room temperature for at least 24 hours before fluorescence measurements were taken. The initial signal was obtained after rapidly pipetting the sample in the cuvette to obtain a stable fluorescence baseline. After acquiring at least 2,000 seconds of the baseline, runs were paused for about 1 minute to add 20 μl of initiator (either 20 μM or 2.5 μM) and allow mixing by rapid pipetting. The final reaction volume was 520 μl for all experiments. The variation in initial fluorescence intensities was about 10% across three experiments.

Figure 1E:
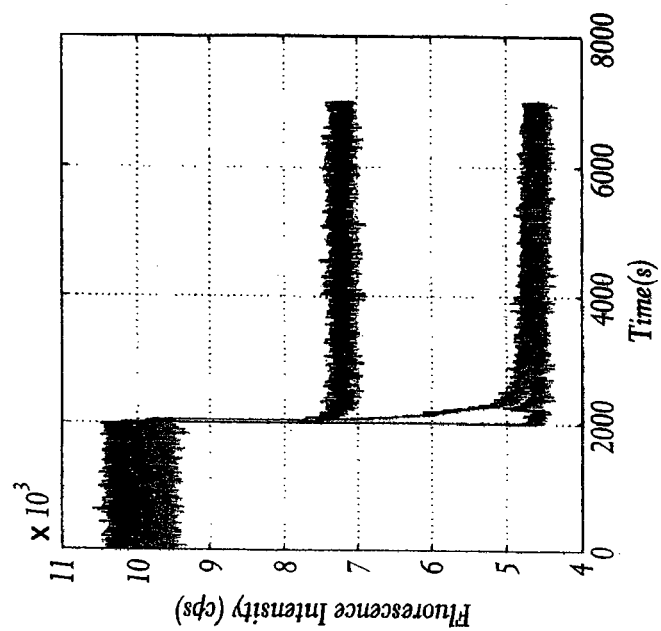
FIG. 1E illustrates HCR kinetics monitored by substituting a fluorescently labeled base in the sticky end of an HCR monomer. Here 2-aminopurine (2AP) was substituted for A (base 3) in the sticky end of H1. The hairpin monomers H1 and H2 did not hybridize prior to triggering by initiator (($H1^{2AP}$+1.2×H2 for 24 hours+0.5×initiator), red). The same quenched baseline was achieved without HCR by adding excess initiator to $H1^{2AP}$ in the absence of H2 ($H1^{2AP}$+4.0× initiator, green). Addition of insufficient initiator to $H1^{2AP}$ provided only partial quenching ($H1^{2AP}$+0.5×initiator (blue), demonstrating that HCR, and not initiator alone, was responsible for exhausting the supply of H12AP monomer.
Figure 1D:
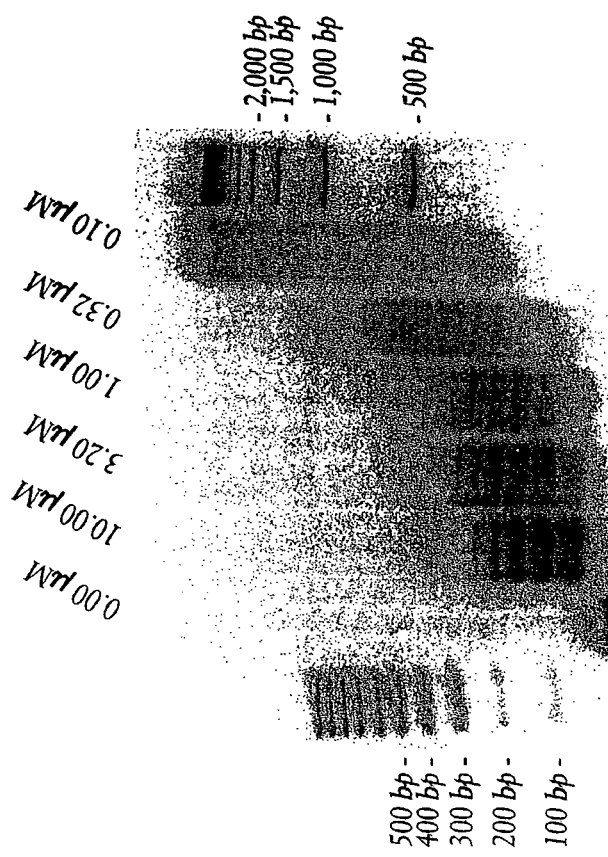
FIG. 1D illustrates the results of an HCR reaction and the effect of initiator concentration on amplification. Lanes 2-7: Six different concentrations of initiator were used (0.00, 10.00, 3.20, 1.00, 0.32 and 0.10 µM, respectively) in a 1 µM mixture of H1 and H2. Lanes 1 and 8 were DNA markers with 100-bp and 500-bp increments respectively.
Figure 2D:
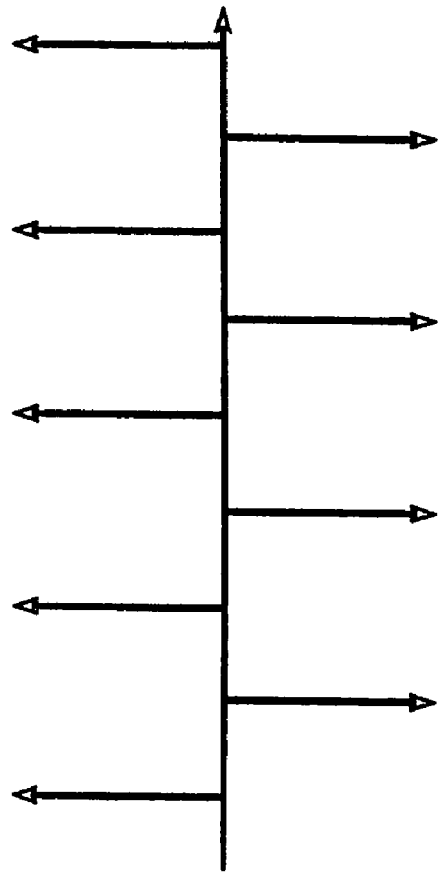
As illustrated in FIG. 2D, the resulting branched polymer has a Q1/Q2 main chain with H1/H2 side chains branching off at each Q2 segment.
Figure 4B:
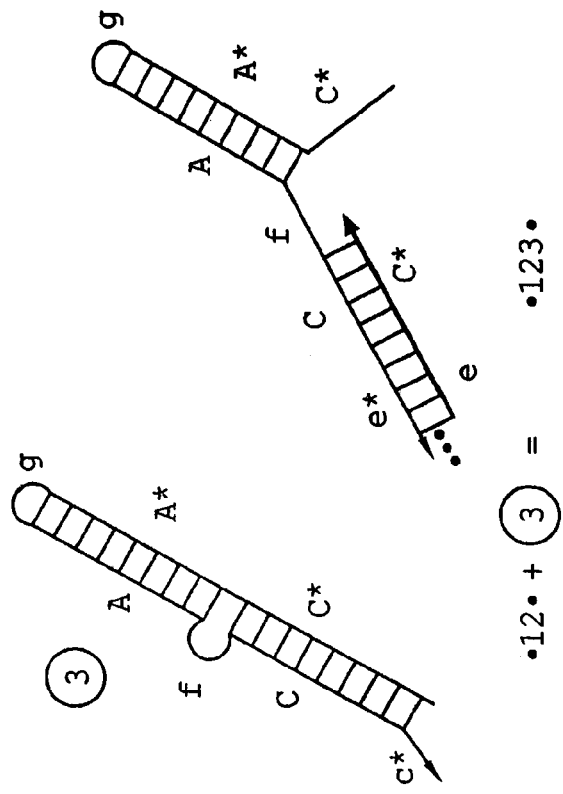
Figure 4A:
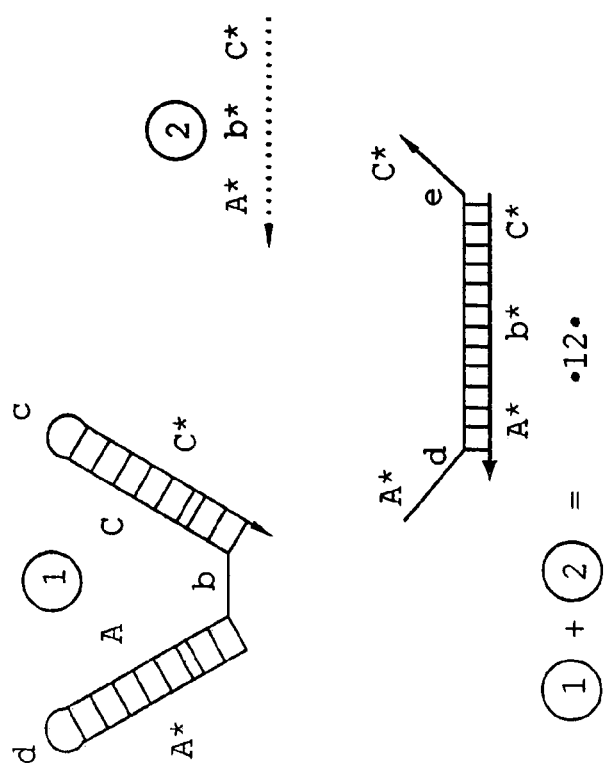
Figure 4E:
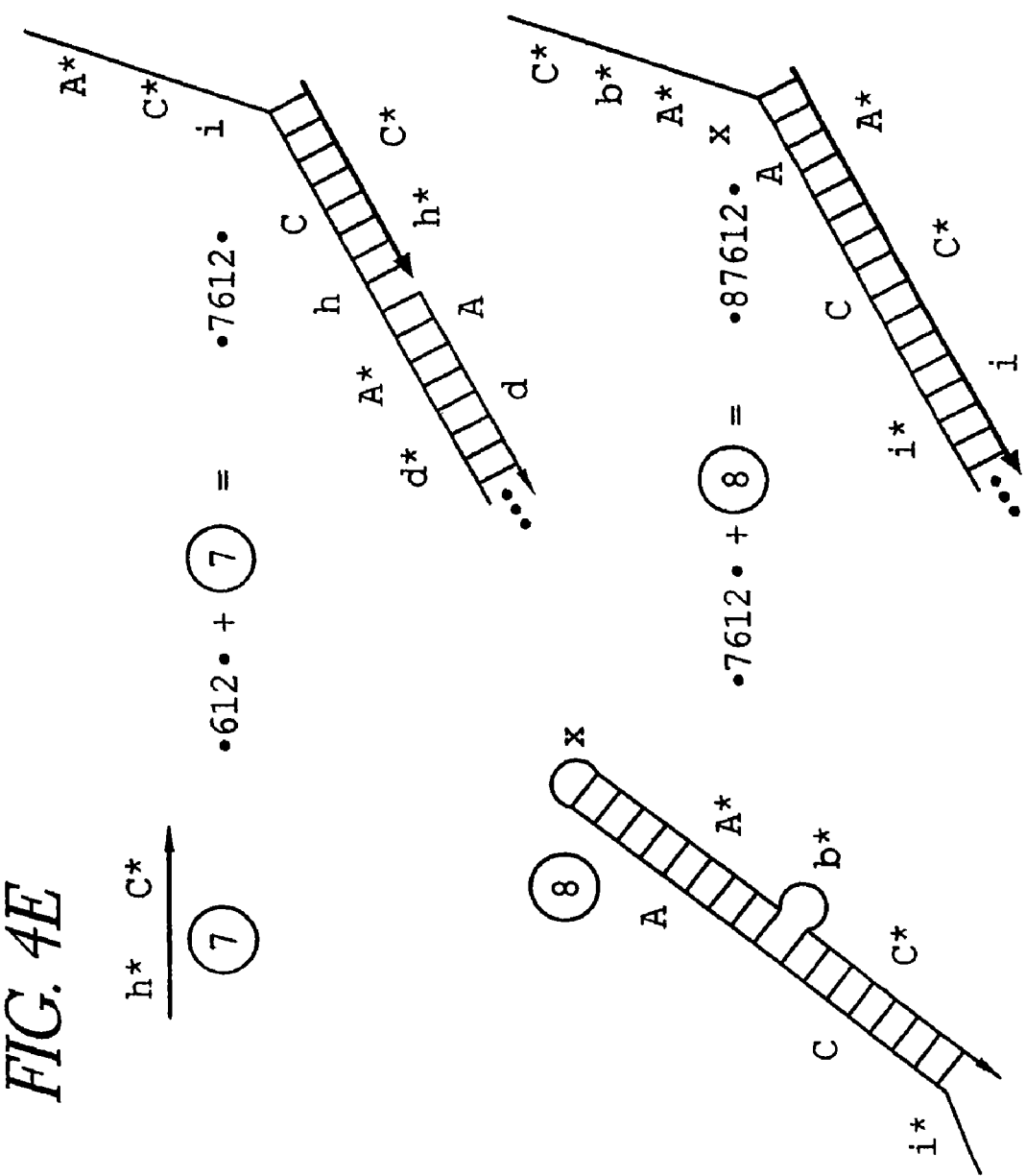

As evidenced by the results presented in FIG. 1E the hairpin monomers H1 and H2 do not hybridize in the absence of initiator. Addition of initiator (I) to the hairpin mixture led to fluorescence quenching via HCR (bottom band from 0 to 2000 seconds, then dropping to middle band from 2000 seconds on)

The same quenched baseline was achieved without HCR by combining $H1^{2AP}$ with excess initiator in the absence of H2 (FIG. 1(E), middle band from 0 to 2000 seconds, then dropping to bottom band from 2000 seconds on). In this case, each initiator molecule caused one fluorescent signaling event by binding to $H1^{2AP}$. With H2 present, HCR performed fluorescent amplification, allowing each initiator molecule to alter the fluorescence of multiple hairpins.

Addition of insufficient initiator to $H1^{2AP}$ provided only partial quenching (FIG. 1(E), top band), demonstrating that HCR, and not initiator alone, was responsible for exhausting the supply of H1$^{2AP}$ monomer.

Although the foregoing invention has been described in terms of certain preferred embodiments, other embodiments will be apparent to those of ordinary skill in the art. Additionally, other combinations, omissions, substitutions and modifications will be apparent to the skilled artisan, in view of the disclosure herein. Accordingly, the present invention is not intended to be limited by the recitation of the preferred embodiments, but is instead to be defined by reference to the appended claims. All references cited herein are incorporated by reference in their entirety.

What is claimed is:

1. A method for detecting an analyte in a biological sample, the method comprising:
   contacting the sample with a probe comprising a target region and an initiation nucleic acid region, wherein the target region is able to specifically bind to the analyte;
   contacting the sample with a first metastable monomer comprising a hairpin loop region and an initiator complement region that comprises a first sticky end and is complementary to the initiation nucleic acid region of the probe; and
   contacting the sample with a second metastable monomer comprising a second sticky end that is complementary to the hairpin loop region of the first monomer,
   wherein the first monomer is labeled with a first fluorophore; and
   detecting the analyte in the sample by measuring fluorescence of the sample.

2. The method of claim 1, wherein the analyte is a nucleic acid.

3. The method of claim 2, wherein the analyte is a gene.

4. The method of claim 3, wherein the analyte is mRNA.

5. The method of claim 3, wherein the target region is complementary to a portion of the nucleic acid.

6. The method of claim 5, wherein the initiation region is complementary to a portion of the analyte binding region.

7. The method of claim 1, wherein the second monomer is labeled with a second fluorophore.

8. The method of claim 7, wherein the first and second fluorophore are different.

9. The method of claim 1, wherein the first monomer comprises a fluorescence quencher.

10. The method of claim 1, wherein the target region comprises an antibody.

11. The method of claim 1, wherein the probe undergoes a conformational change upon biding of the target region to the analyte, and wherein the conformation change makes the initiation region available to bind to the first monomer.

12. The method of claim 1, wherein the first and second metastable monomers are hairpin monomers.

13. The method of claim 1, additionally comprising contacting the sample with a third and fourth metastable monomer.

14. A method of in situ imaging comprising:
   contacting a biological sample with a probe comprising a target region capable of specifically binding an analyte of interest and an initiator region, such that the probe binds to the analyte of interest;
   contacting the biological sample with a first fluorescently labeled metastable monomer comprising a hairpin loop region and an initiator complement region that comprises a first sticky end that hybridizes to the initiator region of the probe; and
   contacting the sample with a second fluorescently labeled metastable monomer comprising a second sticky end that is complementary to the hairpin loop region of the first monomer such that the monomers form a fluorescently labeled polymer tethered to the analyte; and
   detecting the fluorescently labeled polymer.

15. The method of claim 14, wherein the fluorescent label, on at least one of the monomers is quenched prior to formation of the tethered polymer.

16. The method of claim 14, wherein the probe is a triggered probe.

17. The method of claim 16, wherein the initiator region of the triggered probe only becomes available to hybridize to the first monomer when the target region of the probe is bound to the analyte of interest.

18. The method of claim 14, wherein the sample is washed to remove unbound probe prior to contacting with the fluorescently labeled monomers.

* * * * *

UNITED STATES PATENT AND TRADEMARK OFFICE
CERTIFICATE OF CORRECTION

PATENT NO. : 7,727,721 B2  Page 1 of 1
APPLICATION NO. : 11/371346
DATED : June 1, 2010
INVENTOR(S) : Pierce et al.

It is certified that error appears in the above-identified patent and that said Letters Patent is hereby corrected as shown below:

At column 5, approximately line 32, please remove "1" and insert therefore, --I--.

At column 19, approximately line 43, please remove "34:656-665." and insert therefore, --34:656-665--.

At column 20, approximately line 6, please remove "(H1+H2+1;" and insert therefore, --(H1+H2+I;--.

At column 24, approximately line 43, in Claim 15, please remove "label," and insert therefore, --label--.

Signed and Sealed this

Ninth Day of November, 2010

David J. Kappos
*Director of the United States Patent and Trademark Office*